(12) United States Patent
Griess et al.

(10) Patent No.: US 9,239,236 B2
(45) Date of Patent: Jan. 19, 2016

(54) SYSTEM AND METHOD FOR TESTING COMPRESSION PANELS

(71) Applicant: The Boeing Company, Chicago, IL (US)

(72) Inventors: Kenneth H. Griess, Seattle, WA (US); Jack J. Esposito, Auburn, WA (US)

(73) Assignee: The Boeing Company, Chicago, IL (US)

( * ) Notice: Subject to any disclaimer, the term of this patent is extended or adjusted under 35 U.S.C. 154(b) by 232 days.

(21) Appl. No.: 14/184,550

(22) Filed: Feb. 19, 2014

(65) Prior Publication Data

US 2015/0233709 A1    Aug. 20, 2015

(51) Int. Cl.
G01M 5/00 (2006.01)
G01B 11/27 (2006.01)
G01N 3/04 (2006.01)

(52) U.S. Cl.
CPC ............. *G01B 11/272* (2013.01); *G01M 5/005* (2013.01); *G01N 3/04* (2013.01); *G01N 2203/0019* (2013.01); *G01N 2203/0282* (2013.01)

(58) Field of Classification Search
USPC .................................................. 356/600–640
See application file for complete search history.

(56) References Cited

U.S. PATENT DOCUMENTS

| | | | | |
|---|---|---|---|---|
| 3,559,473 A * | 2/1971 | Dudderar | .................. | G01N 3/04 73/818 |
| 3,795,134 A * | 3/1974 | Eichenbrenner | ......... | G01N 3/04 374/50 |
| 5,297,441 A * | 3/1994 | Smith | ...................... | G01N 3/04 73/818 |
| 9,182,330 B2 * | 11/2015 | Kismarton | ............... | G01N 3/02 |

OTHER PUBLICATIONS

U.S. Appl. No. 13/947,050, filed Jul. 20, 2013 and entitled Apparatus, System and Method for Compression Testing of Test Specimens.

* cited by examiner

*Primary Examiner* — Tri Ton
*Assistant Examiner* — Jarreas C. Underwood

(57) ABSTRACT

An alignment apparatus for aligning a test panel with a testing machine may include a laser measuring system and an adjustment mechanism. The laser measuring system may include at least one laser measuring device coupled to a test fixture and/or a testing machine. The laser measuring system may generate laser measurement data representative of an orientation of a test panel relative to a platen and/or a loading axis of the testing machine. The adjustment mechanism may adjust, based on the laser measurement data, a location and/or orientation of the test panel relative to the platen and/or the loading axis in a manner such that the test panel is moved into substantially alignment with the platen and/or the loading axis.

20 Claims, 17 Drawing Sheets

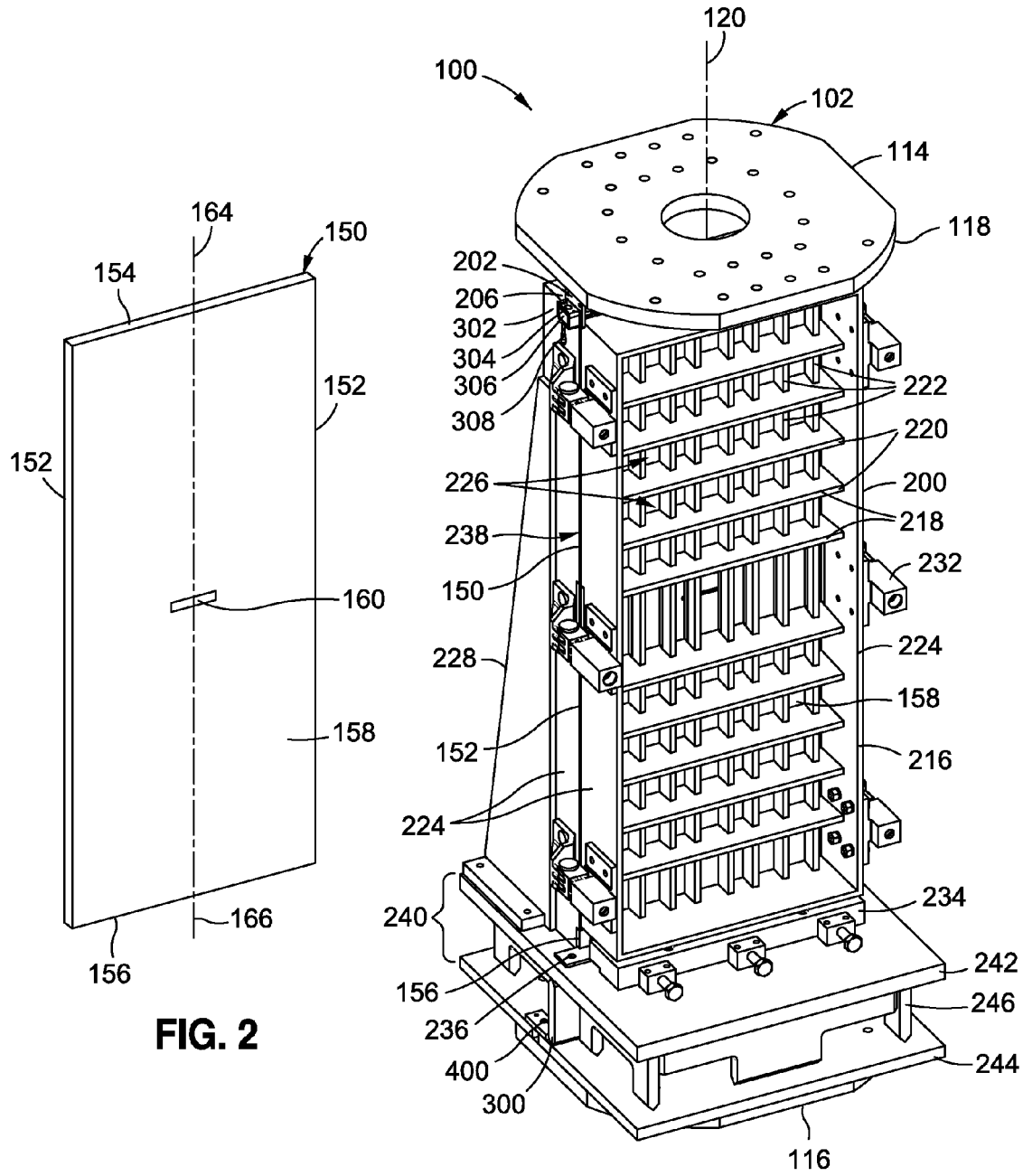

SYSTEM AND METHOD FOR TESTING COMPRESSION PANELS

FIELD

The present disclosure relates generally to structural testing and, more particularly, to a system and method of aligning a test panel for compression testing.

BACKGROUND

The design and development of load-bearing structures often includes the structural testing of components and materials that will be used in such structures. Structural testing provides mechanical property data such as the strength and failure mode of tested components and materials under different environmental conditions such as temperature and relative humidity. The mechanical property data may be used in the design and analysis of a structure such that the structure performs as intended when operating in its service environment.

Compression testing is a type of structural test wherein a compressive test load is applied to a test specimen. The test specimen may be provided as a rectangularly-shaped test panel or test coupon of a predetermined size. The test panel may be formed of composite material (i.e., fiber-reinforced polymer matrix material) and/or metallic material. The test panel may be loaded into a testing machine such that a lower panel edge of the test panel is supported on a base assembly of a test fixture which, in turn, may be supported on a lower platen of the testing machine. A load transmitting interface may be mounted over an upper panel edge of the test panel. The testing machine may include a vertically-movable load head located above the load transmitting interface. The load head may include an upper platen that may be moved downwardly into bearing contact with the load transmitting interface such that a compressive test load may be axially applied to the test panel along a lengthwise (i.e., vertical) direction of the test panel.

For accuracy of testing, the compressive test load is preferably uniformly-distributed across the upper and lower panel edge. However, a test panel may occasionally be provided in a slightly-irregular shape wherein the edges of the test panel are non-perpendicular to one another, or wherein the upper and lower panel edges are non-parallel to one another and resulting in one end of the upper panel edge being higher than an opposite end of the upper panel edge. As a result, the upper platen may initially apply the compressive test load on the higher end of the upper panel edge and the lower end of the test panel may initially be unloaded, resulting in eccentric loading of only one of the opposing ends of the upper panel edge instead of uniformly distributing the compressive test load across the upper panel edge. The non-uniform distribution of the compressive test load may result in premature failure of the test panel and invalid test data.

In conventional practice, the alignment of the test panel may be checked and adjusted by visually searching for light gaps between the load transmitting interface and the upper platen, measuring the width of the gaps using an assortment of feeler gauges, fabricating shims according to the gap measurements, and then installing the shims between the base assembly and the lower platen. The test setup may then be checked for gaps and the process of locating and measuring gaps, fabricating shims, and installing the shims may be repeated in a trial-and-error manner until the gaps between the load transmitting interface and the upper platen are substantially eliminated. Unfortunately, the process of locating and measuring gaps followed by fabricating and installing shims and rechecking for gaps is a time-consuming and labor-intensive process which significantly increases the overall time and expense of structural testing.

As can be seen, there exists a need in the art for a system and method for determining and adjusting the orientation of a test panel in a testing machine and which avoids the time and expensive associated with the conventional trial-and-error process of locating and measuring gaps and installing and fabricating shims.

SUMMARY

The above-noted needs associated with airfoils are specifically addressed by the present disclosure which provides an alignment apparatus for aligning a test panel with a testing machine. The alignment apparatus may include a laser measuring system and an adjustment mechanism. The laser measuring system may include at least one laser measuring device coupled to a test fixture and/or a testing machine. The laser measuring system may generate laser measurement data representative of an orientation of a test panel relative to a platen and/or a loading axis of the testing machine. The adjustment mechanism may be configured to allow for adjusting, based on the laser measurement data, the location and/or the orientation of the test panel relative to the platen and/or the loading axis in a manner such that the test panel is moved into substantially alignment with the platen and/or the loading axis.

In a further embodiment, disclosed is an alignment apparatus for a compression testing system. The compression testing system may have a platen for applying a compressive test load to a test panel. The alignment apparatus may include a load transmitting interface configured to be positioned on a panel edge of a test panel. In addition, the alignment apparatus may include a first and a second laser measuring device disposed on a respective first and second end portion of the load transmitting interface. The first and second laser measuring device may determine a value indicative of a respective first and second distance between the platen and the respective first and second end portion. The alignment apparatus may further include an adjustment mechanism disposed on a base assembly of a test fixture. The alignment apparatus may adjust an orientation of the test panel by raising or lowering a first end portion and/or the second end portion of the load transmitting interface to substantially equalize the first and second distances in a manner such that the load transmitting interface is aligned with the panel edge. In this manner, a compressive test load may be uniformly distributed across a first side edge of the test panel.

Also disclosed is a method of aligning a test panel in a testing machine for applying a compressive test load to a test panel. The method may include mounting a test panel in a testing machine. The method may further include generating, using a laser measuring device coupled to a test fixture and/or the testing machine, laser measurement data representative of an orientation of the test panel relative to a platen and/or a loading axis of the testing machine. The method may additionally include adjusting, based on the laser measurement data, a location and/or orientation of the test panel relative to the platen and/or the loading axis in a manner such that the test panel is substantially aligned with the platen and/or the loading axis.

The features, functions and advantages that have been discussed can be achieved independently in various embodiments of the present disclosure or may be combined in yet other embodiments, further details of which can be seen with reference to the following description and drawings below.

BRIEF DESCRIPTION OF THE DRAWINGS

These and other features of the present disclosure will become more apparent upon reference to the drawings wherein like numbers refer to like parts throughout and wherein:

FIG. 2 is a perspective view of an embodiment of a centrally-notched test panel which may be loaded in the test fixture and to which a compressive test load may be applied by the testing machine to determine a compressive strength of the test panel;

FIG. 3 is a perspective view of an embodiment of a test fixture for supporting the test panel during compression testing;

DETAILED DESCRIPTION

Figure 1:
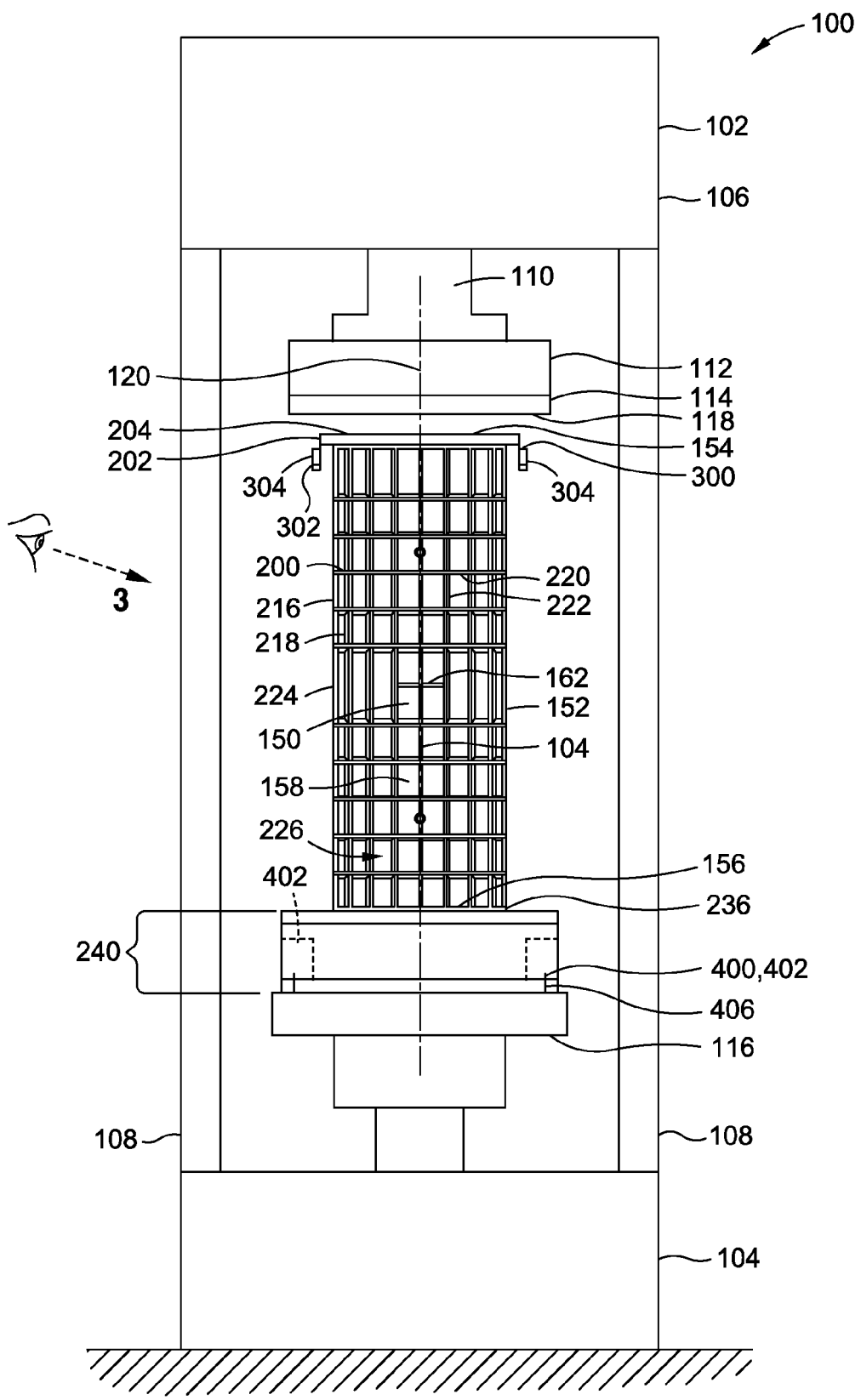
FIG. 1 is a front schematic view of a testing system including a test panel mounted within a test fixture and installed with a universal testing machine for compression testing of the test panel.

Referring now to the drawings wherein the showings are for purposes of illustrating preferred and various embodiments of the disclosure, shown in FIG. 1 is an embodiment of a testing system 100 for compression testing of a test panel 150. The test panel 150 is shown mounted within a test fixture 200 installed in a universal testing machine 102. However, the system and method disclosed herein may be used for testing a test panel 150 without the aid of a test fixture 200. In the embodiment shown, the testing machine 102 may include a base 104 from which one or more vertical posts 108 or columns may extend upwardly to a crosshead 106. The testing machine 102 may include a lower platen 116 mounted to the base 104. The test fixture 200 may be mounted on the lower platen 116. The testing machine 102 may further include a load head 112 mounted on a shaft 110 extending downwardly from the crosshead 106. The load head 112 may be configured to move downwardly at a constant load head travel rate to apply a compressive test load 122 to the test panel 150 along a loading axis 120 of the testing machine 102. The testing machine 102 may include a machine controller (not shown) for controlling the operation of the testing machine 102 such as the head travel rate of the load head 112.

In FIG. 1, the testing machine 102 may include an upper platen 114 mounted to the load head 112. The upper platen 114 may have a platen surface 118 and a width that is at least as wide as the upper panel edge 154 of the test panel 150. In some examples, the upper platen 114 may be coupled to the load head 112 such that the platen surface 118 is oriented normal to the loading axis 120. The upper platen 114 may be fixedly coupled to the load head 112. In some embodiments, the upper platen 114 may be adjustably coupled (e.g., swivelably adjustable) to the load head 112 in a manner allowing the orientation of the platen surface 118 to be adjusted relative to the loading axis 120 to facilitate alignment of the platen surface 118 with the test panel 150 and/or the test fixture 200 based on laser measurement data, as described in greater detail below. During application of the compressive test load 122, the platen surface 118 may be placed in bearing contact with a load transmitting interface 202 that may be mounted on or over an upper panel edge 154 of the test panel 150. In some examples, the test panel 150 may be supported within a test fixture 200 as shown in FIG. 2 and described below. The test fixture 200 may restrain the test panel 150 against out-of-plane deflection during application of the compressive test load 122. The compressive test load 122 may be applied in a manner such that the test panel 150 is loaded in uni-axial compression until failure of the test panel 150 occurs.

Advantageously, the testing system 100 disclosed herein may include an alignment apparatus 300 for adjusting the location and/or orientation of the test panel 150 relative to a platen and/or a loading axis 120 of the testing machine 102 prior to application of the compressive test load 122 on the test panel 150. For example, the alignment apparatus 300 may be configured for adjusting the location and/or the orientation of the test panel 150 relative to the upper platen 114. The alignment apparatus 300 may include a laser measuring system 302 including one or more laser measuring devices 304 that may be coupled to the test fixture 200 and/or to the testing machine 102. The laser measuring system 302 and/or devices 304 may be configured to generate laser measurement data representative of the orientation and/or the location of the test panel 150 relative to the upper platen 114 and/or the loading axis 120 of the testing machine 102. For example, laser measuring devices 304 may be configured to generate laser measurement data representative of an orientation of an upper panel edge 154 of the test panel 150 relative to the upper platen 114 of the testing machine 102. The alignment apparatus 300 may further include one or more adjustment mechanisms 400 configured to adjust the location and/or the orientation of the test panel 150 relative to the platen and/or to the loading axis 120 in a manner such that the test panel 150 is moved into substantial alignment with the platen and/or the loading axis 120.

In some examples, the adjustment mechanism 400 may be mounted to the base assembly 240 of the test fixture 200 and may provide a means for adjusting the vertical height of one or more sides of the base assembly 240 such that the test panel 150/test fixture 200 may be tilted until the centerline 164 and/or the neutral axis 166 of the test panel 150 is substantially aligned with the loading axis 120 of the testing machine 102. The adjustment mechanism 400 may provide a means for adjusting the location and/or orientation of the test panel 150 based on the laser measurement data generated by the laser measurement system 302. For example, the adjustment mechanism 400 may provide a means for aligning the location and/or the orientation of the test panel 150 centerline 164 and/or neutral axis 166 with the location and/or orientation of the testing machine 102 loading axis 120 which may improve the accuracy and repeatability of compression testing of a series of test panels 150. In an embodiment, the adjustment mechanisms 400 may provide a means for orienting a test panel 150 such that the panel upper edge is substantially parallel to the platen surface 118 such that the compressive test load 122 is substantially uniformly distributed across the panel edge of the test panel 150, and thereby avoid loading one side of the upper panel edge 154 which may lead to erroneous or invalid test results.

In FIG. 2, shown is an embodiment of a test panel 150 that may be tested using a testing system 100 and method disclosed herein. The test panel 150 may be a generally rectangular and flat panel member with generally straight sides and may be provided in predetermined or standardized dimensions. For example, in one embodiment, a series of similarly-configured test panels 150 may be provided. Each test panel 150 may have a width and a length of approximately 20 inches by 60 inches, respectively. The test panel 150 may include a horizontally-oriented and centrally-located notch 162 extending through the thickness of the test panel 150. In some embodiments, the notch 162 may have a length of approximately 4 inches and a width of approximately 0.25 inch. In other embodiments, the test panel 150 may be provided in a width and length of approximately 5 inches by approximately 15 inches and may include a horizontally-oriented notch 162 having a length of approximately 1 inch and the width of approximately 0.25 inch. However, the test panel 150 and/or the notch 162 may be provided in any size.

For a test panel 150 formed as a laminate of composite plies comprised of fiber-reinforced polymeric matrix material (e.g., graphite/epoxy, fiberglass, etc.), the test panel 150 may have a thickness of from approximately 0.10 inch to 0.80 inch, although the test panel 150 may be provided in a thickness outside of the 0.10-0.80 inch range. In this regard, the test panel 150 may be provided in any size (e.g., length, width, or thickness), shape, and configuration, without limitation. For example, the test panel 150 may be provided in an arcuate or curved cross-sectional shape (e.g., see FIG. 15) relative to the loading axis 120, as described below. Furthermore, the test panel 150 may include stiffeners 160 (FIG. 15) on one or both of the opposing side surfaces of the test panel 150. The test panel 150 may also be formed of metallic material, or as a hybrid of composite material and metallic material. The test panel 150 may also be formed as a composite sandwich (not shown) having a core of honeycomb or foam sandwiched between a pair of metallic and/or composite face sheets.

During a testing program, a series of similarly-configured test panels 150 may be end-loaded with the compressive test load 122 which may be applied to the upper panel edge 154 by the testing machine 102. The compressive test load 122 may be applied using the load head 112 moving at a constant load head travel rate until failure of the test panel 150 occurs. Compressive force versus load head displacement may be continuously recorded during application of the compressive test load 122 on each one of test panels 150. Strain in the test panel 150 may be measured by a system of strain gauges (not shown) that may be pre-mounted on the test panel 150, and/or by using an optical strain measurement system (not shown). The strain at different locations on the test panel 150 may be continuously recorded in correspondence with the continuous recording of the compressive force and load head displacement. The compressive strength of each test panel 150 may be calculated based on the magnitude of the compressive test load 122 at the point of failure of the test panel 150, and based on the cross-sectional area of the test panel 150.

Referring to FIG. 3, shown is an embodiment of a test fixture 200 for supporting a generally flat, planar test panel 150. As indicated above, the test fixture 200 may be configured to restrain the panel against out-of-plane bending, deflection, and/or buckling during application of the compressive test load 122. The test fixture 200 may include a substantially rigid, non-flexible base assembly 240 which may be mounted on the lower platen 116 of the testing machine 102. The base assembly 240 may be comprised of an upper base plate 242 and a lower base plate 244 interconnected by a series of webs 246. The test fixture 200 may further include a support assembly 216 which may be attached to the base assembly 240. The support assembly 216 may include a pair of support grids 218 which may be coupled together with a test panel 150 captured within a gap 238 formed between the support grids 218. For example, the support grids 218 may be hingedly coupled by a series of hinges 230 on one side of the test fixture 200, and may be latched together using a series of latches 232 on an opposite side of the test fixture 200.

Each one of the support grids 218 may include a plurality of vertical members 222 and a plurality of horizontal members 220 positioned between a pair of frames 224. The horizontal and vertical members 220, 222 may be crisscrossed to create a plurality of windows 226 through which the test panel 150 may be viewed or imaged by an optical strain measuring system (not shown). The test fixture 200 may further include a plurality of crushable core elements (not shown) such as crushable honeycomb sandwich core mounted inside each one of the support grids 218. The core elements may be positioned between the test panel 150 and the support grids 218 to prevent damage to the support grids 218 or the base assembly 240 as result of fracture loads generated by the test panel 150 during a failure of the test panel 150. The base assembly 240 may include a removable and/or replaceable end load element 236 upon which the lower panel edge 156 may be supported. The end load element 236 may protect the base assembly 240 from wear during compression testing. The base assembly 240 may include a grip fixture 234 mounted to the base assembly 240 and configured to hold the lower panel edge 156 during compression testing.

Figure 4:
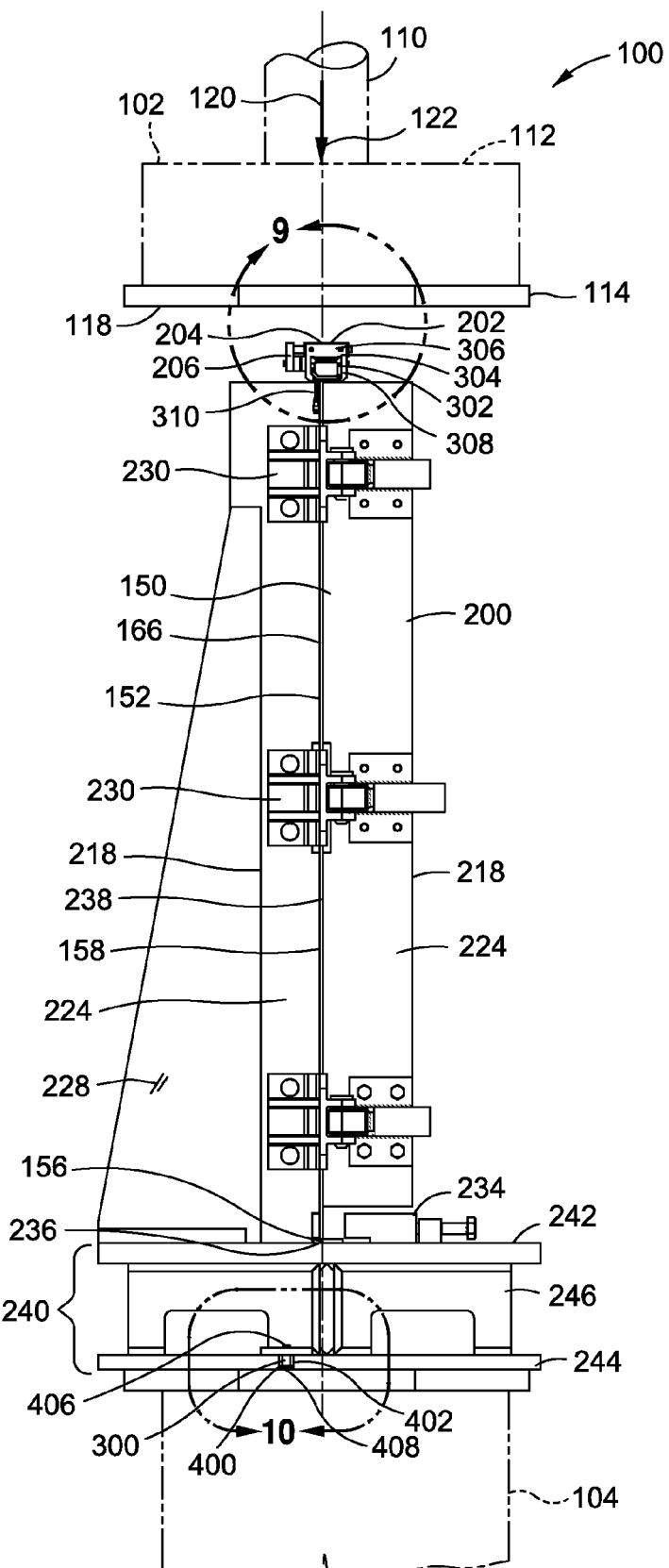
FIG. 4 is a side view of the test fixture of FIG. 2.

In FIG. 4, shown is a side view of the test fixture 200 with the test panel 150 mounted therewithin. The test fixture 200 may include one or more side supports 228 or braces coupling one of the support grids 218 to the base assembly 240 and maintaining the support grids 218 and therefore the test panel 150 in a substantially perpendicular orientation relative to the base assembly 240. The upper panel edge 154 may protrude out of an upper portion of the test fixture 200. A load transmitting interface 202 may be mounted to the upper panel edge 154 to provide an interface with the upper platen 114. One or more laser measuring devices 304 may be mounted on opposite ends 208, 210 of the load transmitting interface 202. Each one of the laser measuring devices 304 may be configured to measure the distance between an end of the load transmitting interface 202 and the surface of the upper platen 114. The test fixture 200 may include one or more adjustment mechanisms 400 disposed on the base assembly 240. As indicated above, each adjustment mechanism 400 may be configured to adjust the orientation of the test panel 150/test fixture 200 by tilting the test panel 150 to raise or lower one or both of the end portions 208, 210 of the load transmitting interface 202.

Figure 5:
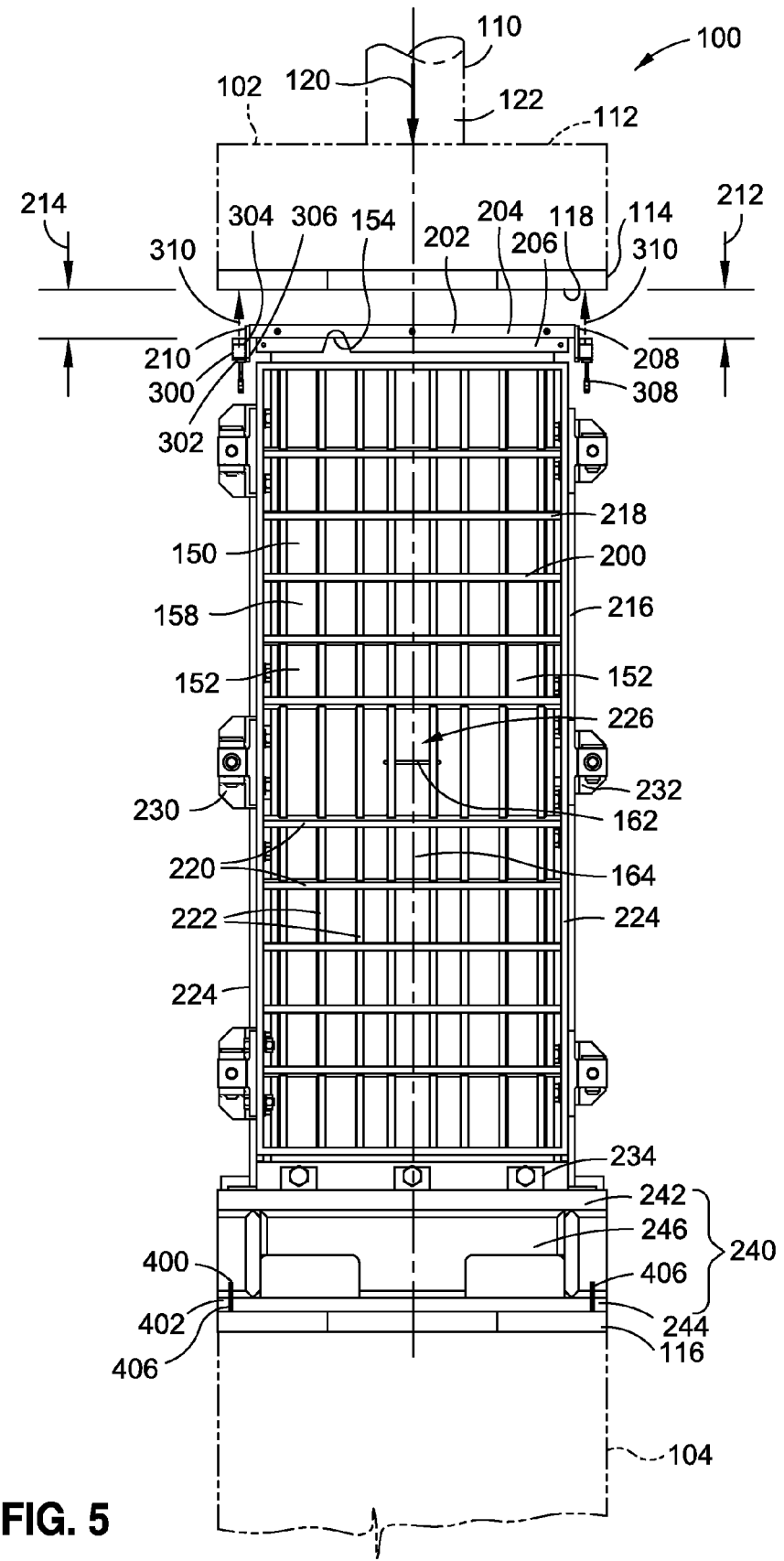
FIG. 5 is a front view of the test fixture of FIG. 2 and illustrating laser measuring devices mounted on opposing ends of a load transmitting interface to be placed in bearing contact with an upper platen of the universal testing machine for compression testing of the test panel.

In FIG. 5, shown is a first laser measuring device 304 and a second laser measuring device 304 positioned on a respective first and second end portion 208, 210 of the load transmitting interface 202. In an embodiment, one or more of the laser measuring devices 304 may be configured as a laser displacement sensor 306. A first and second laser measuring device 304 may be configured to determine a value indicative of the respective first and second distance 212, 214 between the platen surface 118 and the respective first and second end portion 208, 210. Assuming that the upper bearing surface 204 of the load transmitting interface 202 is parallel to the upper panel edge 154, and assuming that the laser measuring devices 304 on each one of the first and second end portions 208, 210 of the load transmitting interface 202 are located at the same distance below the upper bearing surface 204 of the load transmitting interface 202, the difference between the first and second distance 212, 214 may be indicative of a non parallel condition of the platen surface 118 relative to the upper bearing surface 204 of the load transmitting interface 202.

FIG. 5 also illustrates a pair of adjustment mechanisms 400 disposed on opposite sides of the base assembly 240. Each one of the adjustment mechanisms 400 may be configured to raise or lower the corresponding side of the test fixture 200 along a vertical direction 418 resulting in tilting of the test fixture 200. By tilting the test fixture 200, the adjustment mechanisms 400 provide a means for substantially equalizing (e.g., to within approximately 0.002 inch or less) the first and second distances 212, 214 such that the load transmitting interface 202 is aligned with the platen surface 118. In this manner, the bearing surface 204 is substantially parallel to the platen surface 118 such that when a compressive test load 122 is applied to the load transmitting interface 202 by the upper platen 114, the upper platen 114 contacts the length of the load transmitting interface 202 all at one time instead of only contact at one end of the load transmitting interface 202. Due to the upper platen 114 contacting the entire length of the load transmitting interface 202 at one time, the compressive test load 122 is uniformly distributed across the length of the upper panel edge 154 instead of eccentrically loading one side 152 of the test panel 150.

Figure 6:
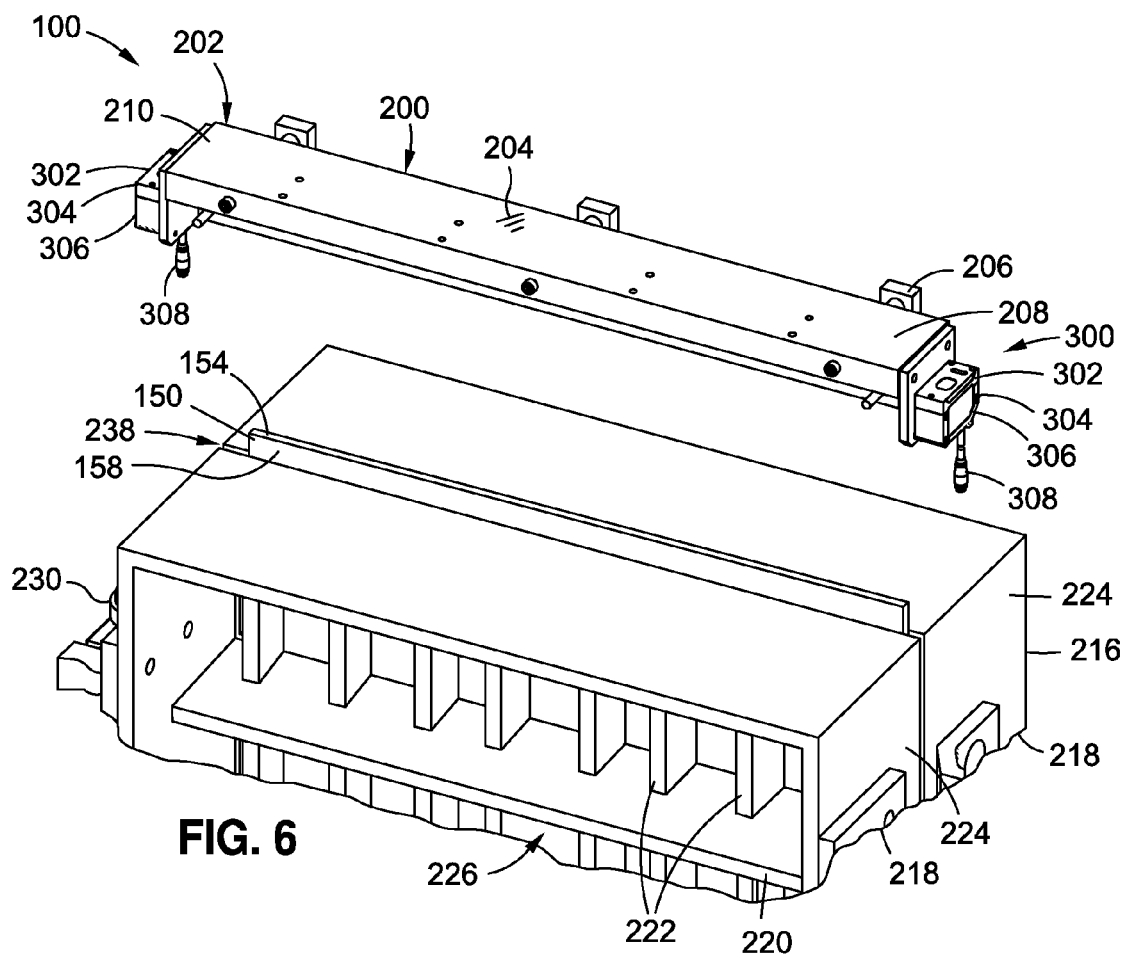
FIG. 6 is an exploded perspective view of the load transmitting interface separated from an upper panel edge of the test panel.
Figure 7:
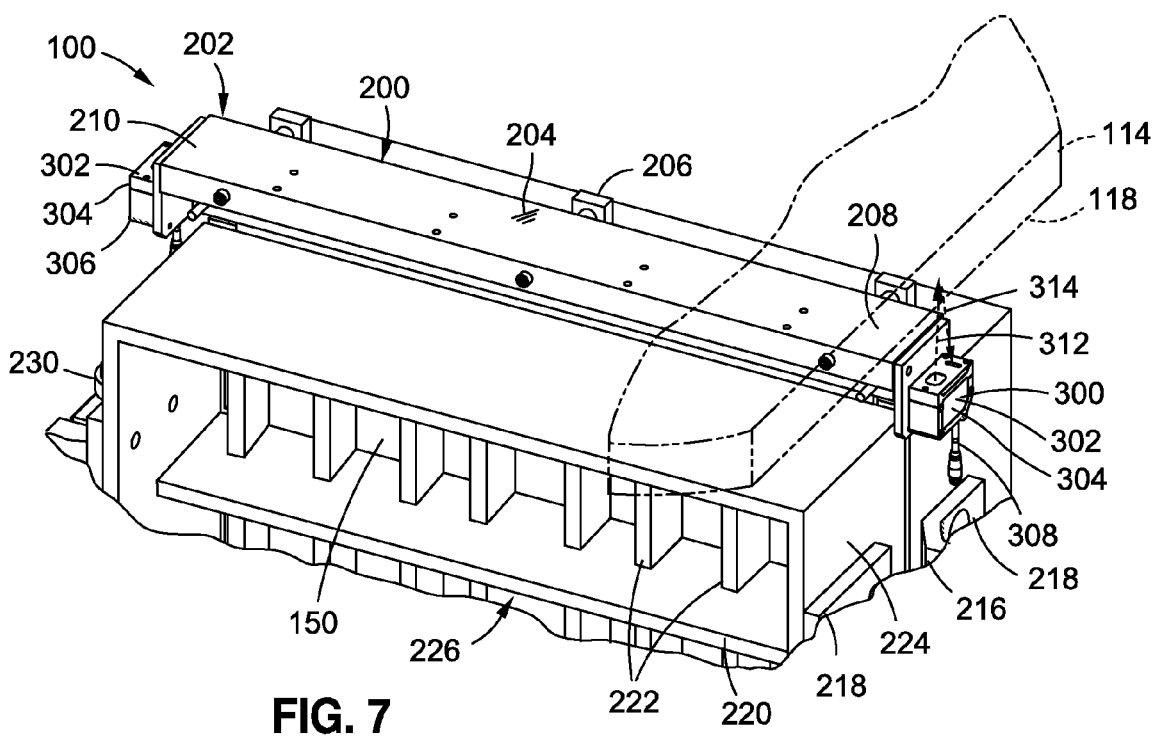
FIG. 7 is a perspective view of the load transmitting interface mounted on the upper panel edge and showing the laser measuring devices emitting a laser beam toward the upper platen for measuring the distance between the load transmitting interface and the upper platen at each end of the load transmitting interface.

FIG. 6-7 show the interconnection of the load transmitting interface 202 with the upper panel edge 154 protruding from the test fixture 200. Laser measuring device 304 may be mounted on each one of the first and second end portions 208, 210 of the load transmitting interface 202. For example, a vertical plate may be fastened to each one of the end portions 208, 210 of the load transmitting interface 202. A laser measuring device 304 may be mounted to each one of the vertical plates. However, laser measuring devices 304 may be mounted at any location on the test fixture 200 for measuring the distance between the upper platen 114 and the upper panel edge 154, and are not limited to being mounted on the opposing end portions 208, 210 of the load transmitting interface 202. The laser measuring devices 304 may be configured as laser displacement sensors 306 for emitting a transmitted beam 310 toward the platen surface 118 of the upper platen 114. The transmitted beam 310 may be emitted from the laser displacement sensor 306 at a slight angle (i.e., non-normal angle) relative to the platen surface 118 of the upper platen 114. The laser displacement sensor 306 may be configured to sense the reflected beam 312 from the platen surface 118. The laser displacement sensors 306 may be coupled via a cable 308 to a data acquisition system (FIG. 13) and/or a processor 320 (FIG. 13) for processing the laser measurement data, as described below.

Figure 8:
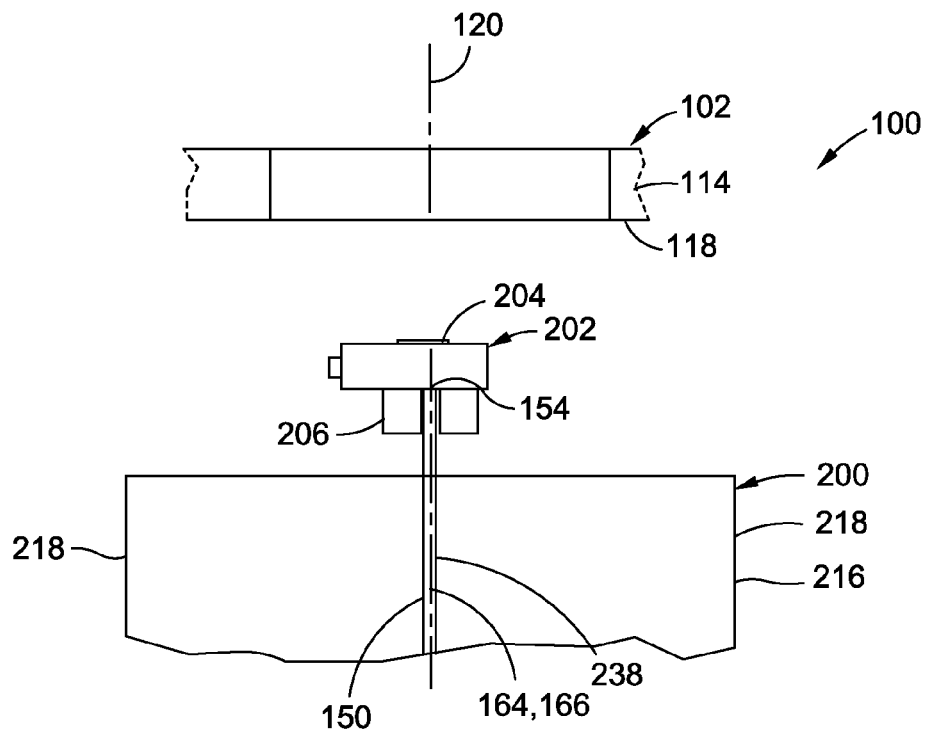
FIG. 8 is a sectional side view of a load transmitting interface mounted on the upper panel edge.

FIG. 8 is a sectional view of the load transmitting interface 202 mounted on the upper panel edge 154. The load transmitting interface 202 includes a bearing surface 204 that is configured to receive the upper platen 114 for applying the compressive test load 122 to the upper panel edge 154. The load transmitting interface 202 may be clamped to the upper panel edge 154 by a clamp member 206. The clamp member 206 may comprise a pair of beam portions extending lengthwise along the upper panel edge 154 and which may be clamped together by mechanical fasteners with the test panel 150 sandwiched between the beam portions. The clamp member 206 may be configured to maintain the lower surface of the load transmitting interface 202 parallel to the thickness of the test panel 150. Likewise, the clamp member 206 may be configured to maintain the bearing surface 204 of the load transmitting interface 202 parallel to the platen surface 118 of the upper platen 114 such that the compressive test load 122 is uniformly applied across the thickness of the upper panel edge 154.

Figure 9:
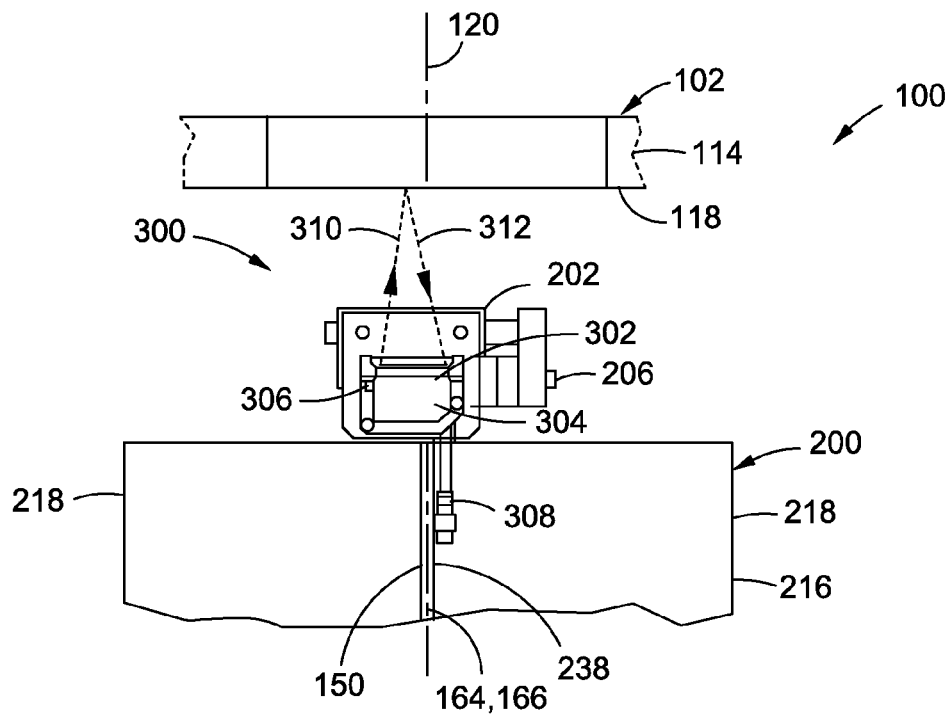
FIG. 9 is a sectional side view of a laser displacement sensor emitting a laser beam toward a platen surface of the upper platen for measuring the distance therebetween.

FIG. 9 is a sectional view of a laser displacement sensor 306 emitting a laser beam toward the platen surface 118 of the upper platen 114 for measuring the distance therebetween. The laser displacement sensor 306 may include a sensor surface such as a charge-coupled device configured to detect the reflected beam 312 from the upper platen 114. The sensor surface may determine the distance from the laser displacement sensor 306 to the platen surface 118 based on the location where the reflected beam 312 strikes the sensor surface. Although the present disclosure describes the laser measurement system 302 as including laser displacement sensors 306, the laser measurement system 302 may include any type non-contact optical sensor, without limitation, capable of determining the distance between the upper platen 114 and the upper panel edge 154 on opposite ends thereof. The laser measurement system 302 may be configured to provide a digital indication for readout of the distance between the upper platen 114 and the load transmitting interface 202 and preferably with a relatively high degree of accuracy such as within 0.002 inch or less.

Figure 10:
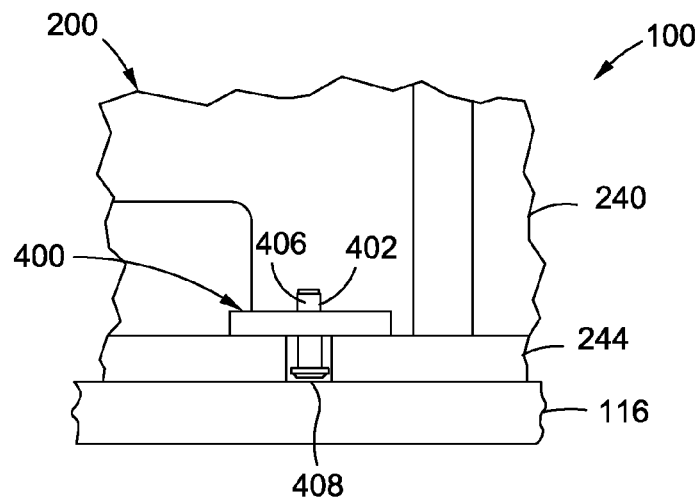
FIG. 10 is a side view of an adjustment mechanism mounted on a base assembly of a test fixture for adjusting the orientation of the test panel relative to the platen and/or loading axis of the testing machine.

FIG. 10 is a side view of an embodiment of an adjustment mechanism 400 mounted on a base assembly 240 of the test fixture 200. The adjustment mechanism 400 may be configured for adjusting the orientation of the test panel 150 relative to the platen and/or loading axis 120 of the testing machine 102. In an embodiment, the adjustment mechanism 400 may be configured as a vertical adjustment mechanism 402 configured to raise or lower a side of the test fixture 200 supporting the test panel 150 as a means to raise or lower the side of the load transmitting interface 202. In this manner, the bearing surface 204 of the load transmitting interface 202 is moved into substantially parallel relation to the platen surface 118 of the upper platen 114. In an embodiment, the adjustment mechanism 400 may be provided as a threaded rod member 406 threadably coupled to the base assembly 240. For example, the threaded rod member 406 may be configured as a hex head bolt or Allen head bolt extending through a plate or bracket 410 fastened to the lower base plate 244 of the base assembly 240. The threaded rod member 406 may include a bearing tip 408 configured to be placed in bearing contact with a lower platen 116.

Figure 11:
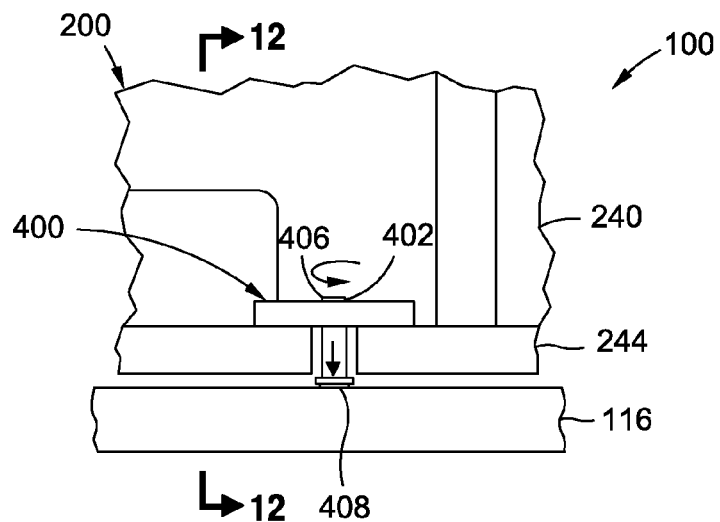
FIG. 11 is a side view of the adjustment mechanism illustrating rotation of a threaded rod member resulting in axially upward displacement of the base assembly relative to a lower platen of the testing machine.

FIG. 11 is a side view of the adjustment mechanism 400 mounted to the base assembly 240 of the test fixture 200 via an attachment bracket 410. Rotation of the threaded rod member 406 relative to the bracket 410 results in axial movement of the threaded rod member 406 causing vertical displacement of the base assembly 240 relative to the lower platen 116 of the testing machine 102. In this manner, the adjustment mechanism 400 may tilt the test panel 150/test fixture 200 such that the upper panel edge 154/load transmitting interface 202 is positioned in parallel relation to the platen surface 118 of the upper platen 114. The reorienting of the test panel 150 may reduce or eliminate gaps between the load transmitting interface 202 and the upper platen 114 and thereby allow for the uniform distribution of the compressive test load 122 across the upper panel edge 154 which may avoid stress concentrations on one end of the upper panel edge 154.

Figure 12:
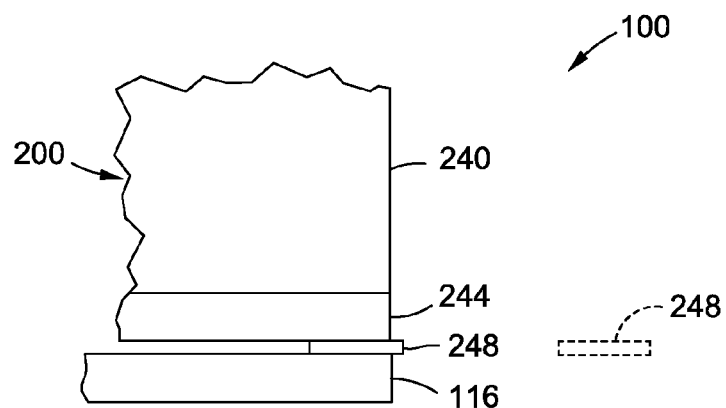
FIG. 12 is a sectional side view of the base assembly illustrating the installation of a shim between the base assembly and the lower platen.

FIG. 12 is a side view of the base assembly 240 showing the installation of a shim 248 between the base assembly 240 and the lower platen 116. Following the adjustment of the adjustment mechanism 400 to orient the upper panel edge 154 and/or load transmitting interface 202 into alignment with (e.g., parallel to) the platen surface 118 of the upper platen 114, the gap 238 between the base assembly 240 in the lower platen 116 may be measured in a series of shims 248 may be fabricated. Additions may be installed to maintain the orientation of the test panel 150/test fixture 200 during the application of the compressive test load 122 of the test panel 150. Advantageously, in an embodiment, the laser displacement sensors 306 may generate a digital readout of the distances between opposing end portions 208, 210 of the load transmitting interface 202. The difference between the values (e.g., distances) displayed on the digital readout of laser displacement sensors 306 may be used to determine an appropriate thickness of the shims 248 to be installed between the base assembly 240 and the lower plaque on at least one side of the test fixture 200.

Figure 13:
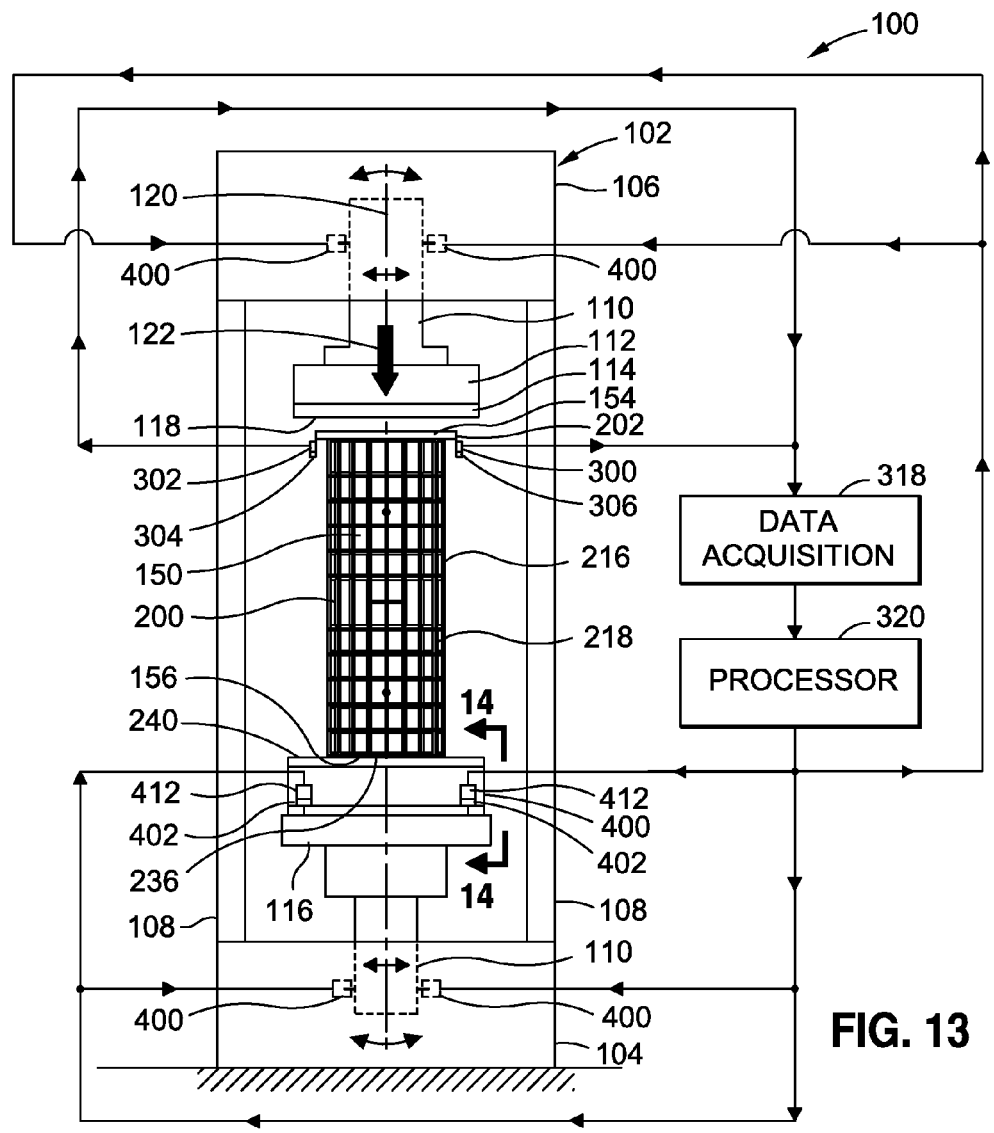
FIG. 13 is a front view of an embodiment of a testing system including a data acquisition device and a processor for receiving laser measurement data from the laser measuring devices and generating one or more commands transmitted to one or more motorized adjustment mechanisms for adjusting the location and/or orientation of the test panel.

FIG. 13 is a front schematic view of an embodiment of a testing system 100 enabling autonomous are semi-autonomous adjustment of the test panel 150 relative to the testing machine 100. In the embodiment shown, the testing system 100 may include a data acquisition device 318 and/or a processor 320 communicatively coupled to one or more of the laser measuring devices 304. The data acquisition device 318 and/or processor 320 may receive laser measurement data from one or more of the laser measuring devices 304. The laser measuring devices 304 may be configured to measure the distances 212, 214 (FIG. 5) between the load transmitting interface 202 at each end portion 208, 210 (FIG. 5) and the upper platen 114 and determine the difference between the distances 212, 214. As indicated above, the difference between the distances 212, 214 may potentially represent a misalignment of the bearing surface 204 of the load transmitting interface 202 with the platen surface 118 of the upper platen 114. The data acquisition device 318 may transmit the laser measurement data to the processor 320.

In FIG. 13, the testing system 100 may include one or more motorized adjustment mechanisms 400 for adjusting the location and/or the orientation of the test panel 150 relative to a platen 114, 116 and/or the loading axis 120 of the testing machine 102. For example, each one of the adjustment mechanisms 400 may include a motor 412 that may be operatively coupled to a rod member 406 having a bearing tip 408. The motor 412 may include a motor controller 414 which may be communicatively coupled to the processor 320 and receive commands from the processor 320 based upon the laser measurement data. The adjustment mechanisms 400 may be mounted such that the bearing tips 408 are in contact with a component of the testing machine 102 or test fixture 200. Each motor 412 may be operated in a manner to adjust the axial position of the bearing tip 408 as a means to change the lateral position, vertical position, and/or angular orientation of the component (e.g., the test fixture 200, or a shaft 110 or platen 114, 116 of the testing machine 102, etc.) to be adjusted, as described in greater detail below. In some examples, the rod member 406 may be a threaded rod member 406 that may be rotatably driven by the motor 412 to axially displace the bearing tip 408 of the rod member 406, as discussed in greater detail below regard to FIG. 14.

In some examples, the adjustment mechanisms 400 may be configured to adjust the position and/or an orientation of the test fixture 200 relative to the platen and/or the loading axis 120 based upon commands issued by the processor 320. In other examples, the adjustment mechanisms 400 may receive commands from the processor 320 to adjust the position and/or the orientation of a platen 114, 116 and/or the loading axis 120 relative to the testing machine 102. For example, one or more adjustment mechanisms 400 may be mounted to the base assembly 240 of the test fixture 200 for autonomously adjusting the tilt angle of the test fixture 200 in response to commands received from the processor 320 based upon the laser measurement data.

In FIG. 13, one or more of the adjustment mechanisms 400 may be operatively engaged to the shaft 110 on the lower portion of the testing machine 102. In some examples, one or more of the adjustment mechanisms 400 may be located on one or more sides of the shaft 110 that extends into the testing machine base 104. The adjustment mechanisms 400 in the testing machine base 104 may be configured to adjust the lateral position of the shaft 110 in response to commands generated by the processor 320. As indicated above, the shaft 110 in the lower portion of the testing machine 102 may support the lower platen 116 which, in turn, may support the test fixture 200. In some embodiments, the adjustment mechanisms 400 in the testing machine base 104 may be configured to adjust the angular orientation of the shaft 110. By using the adjustment mechanisms 400 to adjust the angular orientation of the shaft 110, the angular orientation of the lower platen 116 may be adjusted which may cause the test fixture 200 to tilt such that the upper panel edge 154 (FIG. 9) is moved into substantially parallel alignment with the platen surface 118 (FIG. 9) of the upper platen 114. The adjustment mechanisms 400 in the testing machine base 104 may also be configured to adjust the lateral position and/or angular orientation of the shaft 110 in a manner such that the neutral axis 166 and/or vertical centerline 164 of the test panel 150 is moved into substantial alignment with the loading axis 120 of the testing machine 102.

In some examples, one or more of the adjustment mechanisms 400 may be located in an upper portion of the testing machine 102. For example, FIG. 13 illustrates a pair of adjustment mechanisms 400 operatively engaged to the shaft 110 extending upwardly into the cross head 106 of the testing machine 102. In the embodiment shown, the adjustment mechanisms 400 may be located on the sides of the shaft 110 that extends into the cross head 106. The adjustment mechanisms 400 in the cross head 106 may be configured to adjust the lateral position of the shaft 110 such that the compressive test load 122 is substantially aligned with the neutral axis 166 and/or the vertical centerline 164 of the test panel 150. In other examples, the adjustment mechanisms 400 in the cross head 106 may be configured to adjust the angular orientation of the shaft 110 such that the loading axis 120 is aligned with the neutral axis 166 and/or the vertical centerline 164 of the test panel 150. The adjustment mechanisms 400 may also be configured to adjust the angular orientation of the shaft 110 and the upper platen 114 which is attached to the shaft 110. By using the adjustment mechanisms 400 to adjust the angular orientation of the upper platen 114, the platen surface 118 (FIG. 9) of the upper platen 114 may be moved into substantially parallel alignment with the upper panel edge 154 of the test panel 150.

Figure 14:
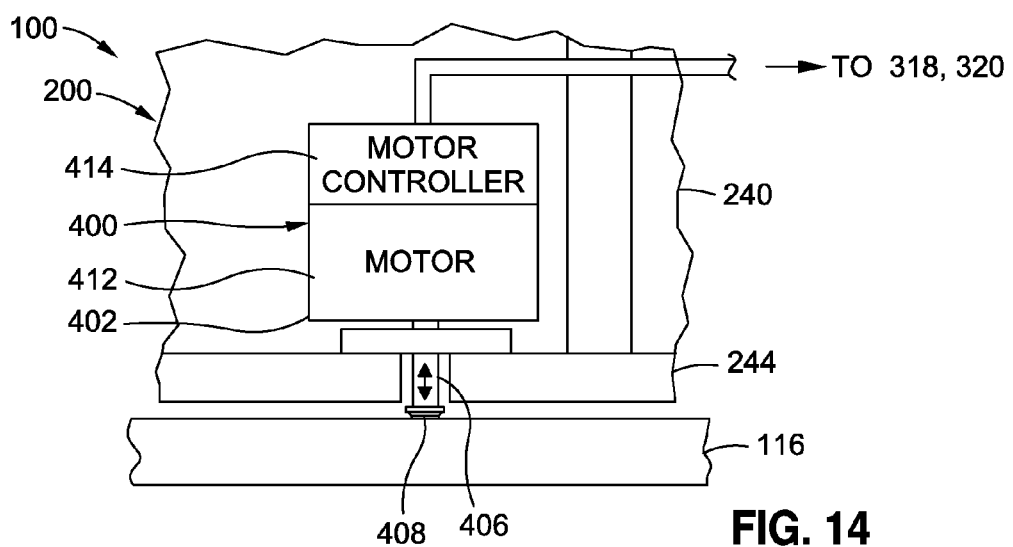
FIG. 14 is a side view of an example of a motorized adjustment mechanism including a motor and a motor controller communicatively coupled to the processor for receiving commands from the processor for automatic adjustment of the test panel based upon laser measurement data received by the processor from the laser measuring devices.

FIG. 14 illustrates a side schematic view of an example of a motorized adjustment mechanism 400. In the embodiment shown, the threaded rod member 406 of the adjustment mechanism 400 may be operatively coupled to the motor 412 which may be controlled by a motor controller 414 communicatively coupled to the processor 320. The processor 320 may command one or more of the motorized adjustment mechanisms 400 to adjust the location and/or orientation of the test panel 150 and/or test fixture 200 into substantial alignment with the testing machine 102. For example, the processor 320 may command the motor controller 414 to operate the motor 412 to rotate the threaded rod member 406 causing vertical displacement of one side of the base assembly 240 relative to the lower platen 116 until the load transmitting interface 202 is moved into substantially parallel alignment with the upper platen 114. It should be noted that the configuration of the adjustment mechanisms 400 is not limited to a rotatable threaded rod member 406 threadably engaged to the base assembly 240. For example, an adjustment mechanism 400 may include an axially-movable rod member instead of a rotatable rod member. In this regard, the adjustment mechanisms 400 may be provided in any configuration, without limitation, capable of adjusting the location and/or orientation of the test panel 150 and/or test fixture 200. For example, the adjustment mechanisms 400 may be configured as a hydraulic actuator, an electromechanical actuator, or any other type of mechanism, device, or system configured to adjust the location and/or orientation of the test fixture 200 and/or test panel 150 relative to the testing machine 102.

It should also be noted that in any of the embodiments disclosed herein, after the test panel 150 is aligned and the compressive test load 122 is initially applied to the test panel 150, one or more of the laser measuring devices 304 may continue to scan the test panel 150 and/or test fixture 200, and/or may continue to measure distances between the testing machine 102 and the test panel 150 and/or test fixture 200, and transmit laser measurement data to the data acquisition device 318. The data acquisition device 318 may be configured to sample the laser measurement data at a predetermined frequency such as every several seconds, depending on the load head travel rate and/or other testing parameters, as indicated above. In this manner, the data acquisition device 318 may provide a means for measuring and/or recording changes in the location and/or orientation of the test panel 150 relative to the testing machine 102 during the process of compressively loading the test panel 150. The data acquisition device 318 may be configured to periodically or continuously sample the laser measurement data throughout the compressive loading process up to failure of the test panel 150. The laser measurement data may be correlated with the recording of the compressive force versus load head displacement, and the recording of strain in the test panel 150 during application of the compressive test load 122.

Figure 15:
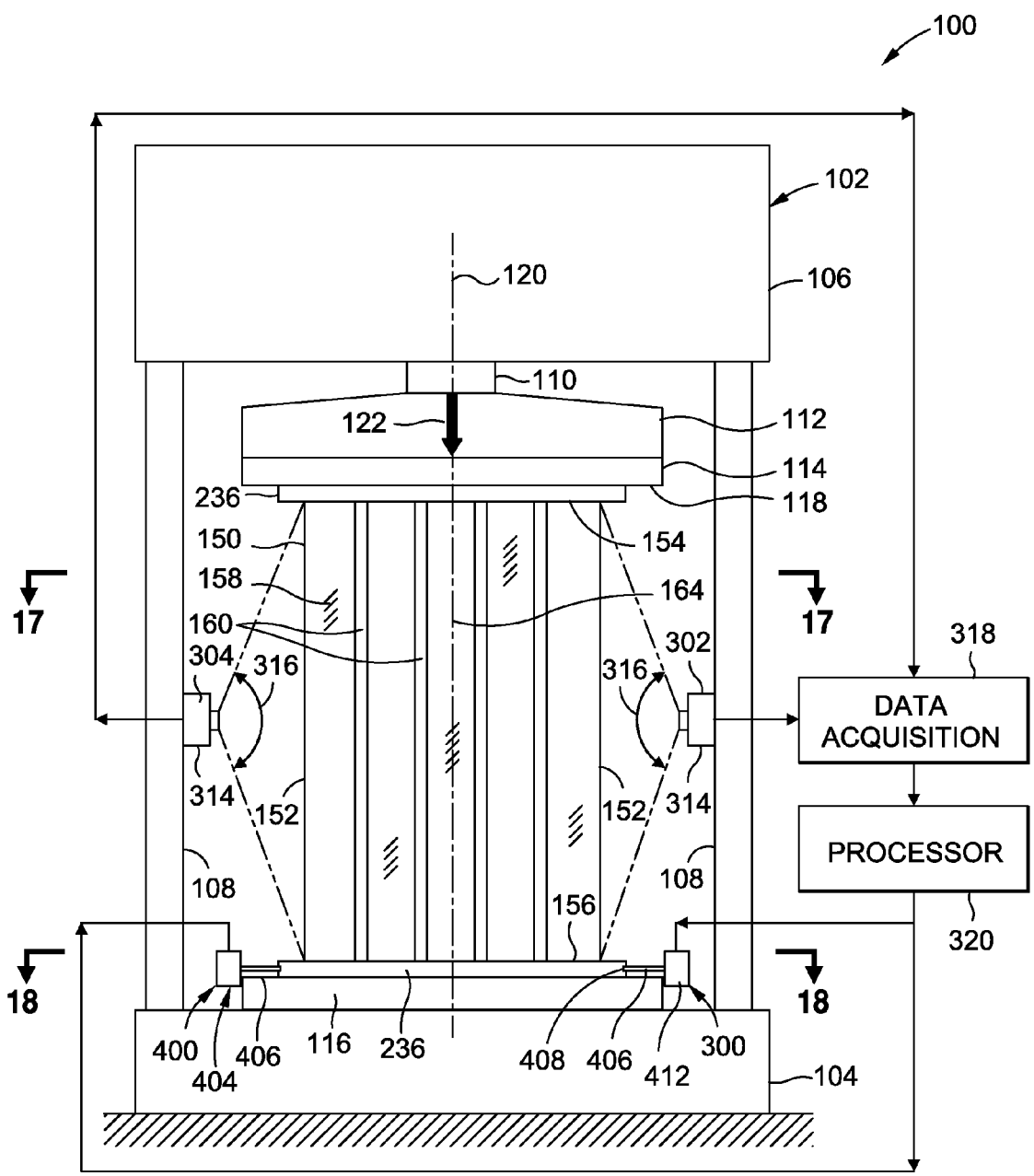
FIG. 15 is a front view of an embodiment of a testing system including a plurality of laser scanners for scanning a surface geometry of the test panel and/or test fixture, and generating scanning data received by a processor for determining a neutral axis and/or centerline of the test panel relative to the loading axis.

FIG. 15 is a schematic view of an embodiment of a testing system 100 having a plurality of laser scanners 314 and including one or more adjustment mechanisms 400. A test panel 150 and/or a test fixture 200 may be mounted within a universal testing machine 102 similar to the testing machine 102 illustrated in FIG. 1 and described above. The test panel 150 may include an upper panel edge 154 and a lower panel edge 156. A lower end load element 236 may be positioned between a lower panel edge 156 of the test panel 150 end a lower platen 116 of the testing machine 102. An upper end load element 236 may be positioned between the upper panel edge 154 of the test panel 150 and an upper platen 114 of the testing machine 102 during application of the compressive test load 122. In an embodiment, one or more laser scanners 314 may be mounted to the testing machine 102 such as on at least one of the vertical posts 108 of the testing machine 102. The laser scanners 314 may be communicatively coupled to the data acquisition device 318 which may be configured to receive scanning data from the plurality of laser scanners 314. The laser scanners 314 may be configured to scan through a scan angle 316 and scan the surface geometry of the test panel 150 and/or a test fixture 200 during the process of checking and aligning the test panel 150 with this testing machine 102. In addition, the laser scanners 314 may be configured to continuously scan the test panel 150 and/or test fixture 200 during application of the compressive test load 122 on the test panel 150 to record any changes in the location and/or orientation of the test panel 150. During application of the compressive test load 122, the data acquisition device 318 may be configured to sample the laser scanning data at a predetermined data sampling rate while simultaneously sampling the strain data from the test panel, the compressive test load data, and the load head travel data.

In FIG. 15, although a test fixture 200 is not shown, the test panel 150 may be mounted within a test fixture 200 which may be configured to support the test panel 150 in a substantially vertical orientation and/or may be configured to restrain the test panel 150 against out-of-plane bending, deflection, and/or buckling during application of the compressive test load 122. The test fixture 200 may be configured such that the test panel 150 is non-visible, partially-visible, or completely visible when mounted within the test fixture 200. A partially visible or completely visible test panel 150 within the test fixture 200 may allow an optical strain measurement system (not shown) to measure and record strain in the test panel 150 during application of the compressive test load 122. The laser scanners 314 may be configured to scan the surface geometry such as the surfaces and the edges of the test fixture 200 and/or the test panel 150. The laser scanners 314 may be configured to generate scanning data representative of the surface geometry of the test panel 150 and/or test fixture 200 and generate scanning data (e.g., a point cloud) representative of the surface geometry.

In an embodiment, the processor 320 may be configured to receive the scanning data from the laser scanners 314 and determine a location and/or an orientation of the test panel 150 and/or test fixture 200 relative to the testing machine 102. For example, based on a known relationship between the test panel 150 and the test fixture 200, the processor 320 may be configured to determine the location and/or orientation of the upper panel edge 154, the centerline 164, and/or the neutral axis 166 of the test panel 150 relative to the platen and/or the loading axis 120 of the testing machine 102. In an embodiment, the processor 320 may be configured to generate digital data or values (e.g., distance values, angular values) representative of the misalignment of the test panel 150 and/or test fixture 200 relative to the upper platen 114 and/or loading axis 120 of the testing machine 102. Based on the data (e.g. values) generated by the processor 320, the adjustment mechanisms 400 may be manually adjusted such as by rotating the threaded rod members 406 to raise and/or lower one or both sides 152 of the test panel 150 and/or test fixture 200 until the test panel 150 is aligned with the upper platen 114 and/or loading axis 120.

Referring still to FIG. 15, in some examples, one or more of the adjustment mechanisms 400 may be motorized and may be communicatively coupled to the processor 320. For example, in a non-limiting embodiment, an adjustment mechanism 400 may include a motor 412 having a motor controller 414 which may be communicatively coupled to the processor 320. The motor 412 may be operatively coupled to a threaded rod member 406 mounted on the base assembly 240 as described above. The processor 320 may be configured to generate commands that may be transmitted to the motor 412 or the motor controller 414 of one or more adjustment mechanisms 400 for automatically adjusting the location and/or orientation of the test panel 150 relative to the testing machine 102 based on the laser measurement data generated by the laser scanners 314. For example, as indicated above, one or more laser scanners 314 may generate laser measurement data representative of the location and/or orientation of the centerline 164 and/or neutral axis 166 of the test panel 150 relative to the location and/or orientation of the loading axis 120 of the testing machine 102.

The processor 320 may generate a command based on the laser measurement data to operate the motor 412 of one or more adjustment mechanisms 400 in a manner such that the centerline 164 and/or neutral axis 166 of the test panel 150 is moved into substantial alignment with the loading axis 120 of the testing machine 102. In some examples, the processor 320 may automatically generate and transit a command to the motors 412 of one or more of the adjustment mechanisms 400. In other examples, the processor 320 may generate a command to one or more of the adjustment mechanisms 400 after manual prompting by a technician. For example, the processor 320 may display visual or digital data indicating the extent of the misalignment of the test panel 150 and/or test fixture 200 with the loading axis 120. A technician may then manually prompt the processor 320 to generate and transmit the commands to the adjustment mechanisms 400 to reorient the test panel 150 and/or test fixture 200 into alignment with the loading axis 120. In any of the examples described herein, the processor 320 may also be configured to automatically generate and transmit a command to the adjustment mechanisms 400 upon determining that the upper platen 114 is misaligned or is non-parallel to the load transmitting interface 202 or to the upper panel edge 154 of the test panel 150.

Figure 16:
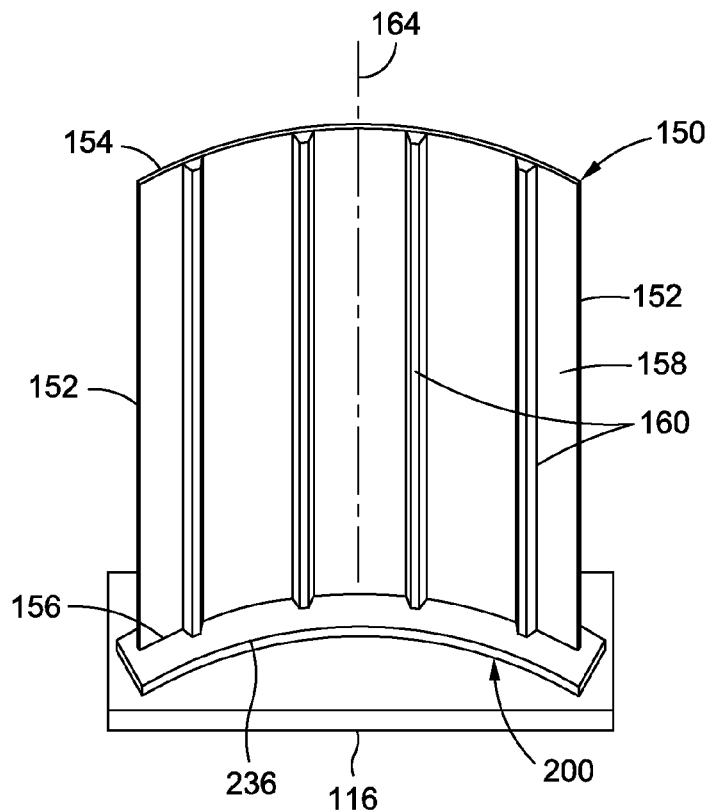
FIG. 16 is a schematic perspective view of a curved test panel having stiffeners and wherein laser scanners may scan a surface geometry of the test panel to determine the neutral axis and/or centerline of the test panel for aligning with the loading axis.

FIG. 16 is a schematic view of an example of a test panel 150 that may be aligned in a testing machine 102 using the alignment apparatus 300 and method disclosed herein. The test panel 150 may include a skin panel 158 formed into a curved cross-sectional shape. One or more stiffeners 160 may be coupled to at least one of the side surfaces of the skin panel 158. The skin panel 158 may be a laminate of a plurality of composite plies (e.g., graphite/epoxy, fiberglass, etc.) arranged in a ply stacking sequence. The stiffeners 160 may extend in an axial direction along the length of the skin panel 158 and may also be formed of composite material and may be co-cured or co-bonded to one or both side surfaces of the test panel 150. However, as indicated above, the skin panel 158 may be formed of metallic material, or as a combination of metallic and composite material. The skin panel 158 may include additional stiffening or reinforcing structure such as circumferential frame segments (not shown). Regardless of the size, shape, or configuration of the test panel 150, the test panel 150 may be mounted in the testing machine 102, and the laser scanners 314 may scan the surface geometry of the test panel 150 to determine the location and/or orientation (e.g., the centerline 164 and/or a neutral axis 166) of the skin panel 158 relative to the testing machine 102. The processor 320 may determine the location and/or orientation of the centerline 164 and/or the neutral axis 166 of the test panel 150 based on the scanning data.

Figure 17:
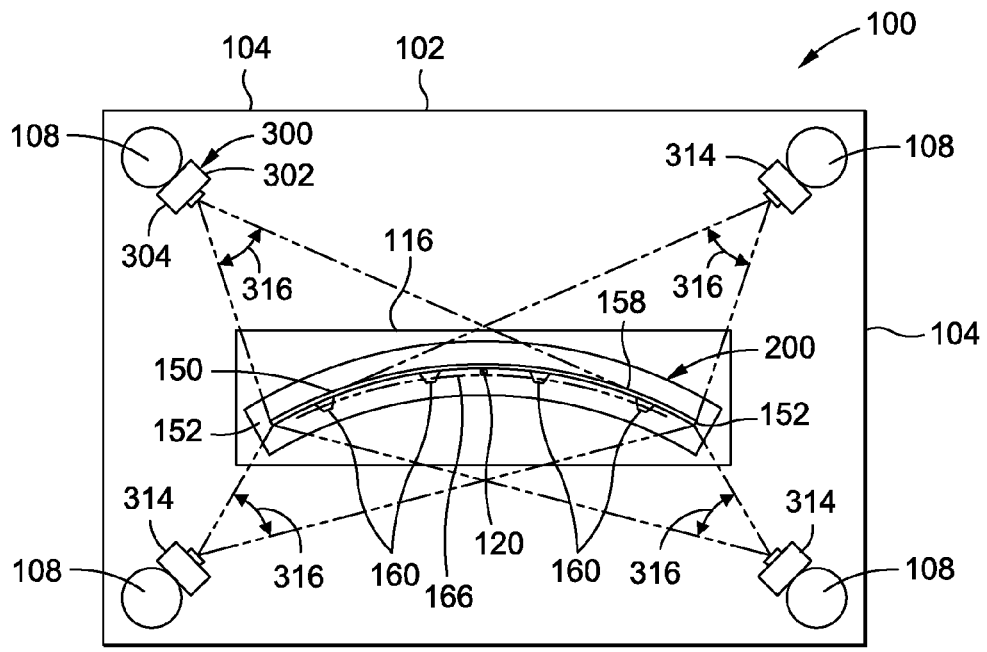
FIG. 17 is a top schematic view of an embodiment of the testing system taken along line 17 of FIG. 15 and showing a plurality of laser scanners mounted on vertical posts of the testing machine for scanning the surface geometry of a test panel and/or test fixture.

FIG. 17 is a top schematic view of an embodiment of the testing system 100 showing an arrangement of laser scanners 314 mounted on the vertical posts 108 of the testing machine 102. Although four (4) laser scanners 314 are shown, any number of laser scanners 314 may be included and may be mounted at any location on the testing machine 102. The laser scanners 314 may optionally be mounted at locations off of the testing machine 102 such as on the floor, walls, or other supporting structure at the location (e.g., a test lab) where compression testing may be performed. The laser scanners 314 may scan the surface geometry of the test panel 150 and/or the test fixture 200. The scanning data may be received at a data acquisition device 318 (FIG. 14) and/or at a processor 320 that may be coupled to the laser scanners 314 In an embodiment, the processor 320 may configured to determine the orientation of the test panel 150 relative to the testing machine 102 using the scanning data. For example, the processor 320 may use the scanning data to generate a point cloud of the test panel 150 and determine the location and orientation of the longitudinal centerline 164 and/or the neutral axis 166 of the test panel 150 relative to a feature of the test panel 150 such as a side 152 edge or the upper panel edge 154 of the test panel 150. For a test panel 150 having stiffeners 160, the neutral axis 166 may be offset from the mid-plane of the skin panel 158. Advantageously, the processor 320 may be configured to determine the location of the neutral axis 166 of a test panel 150 having stiffeners 160.

Figure 18:
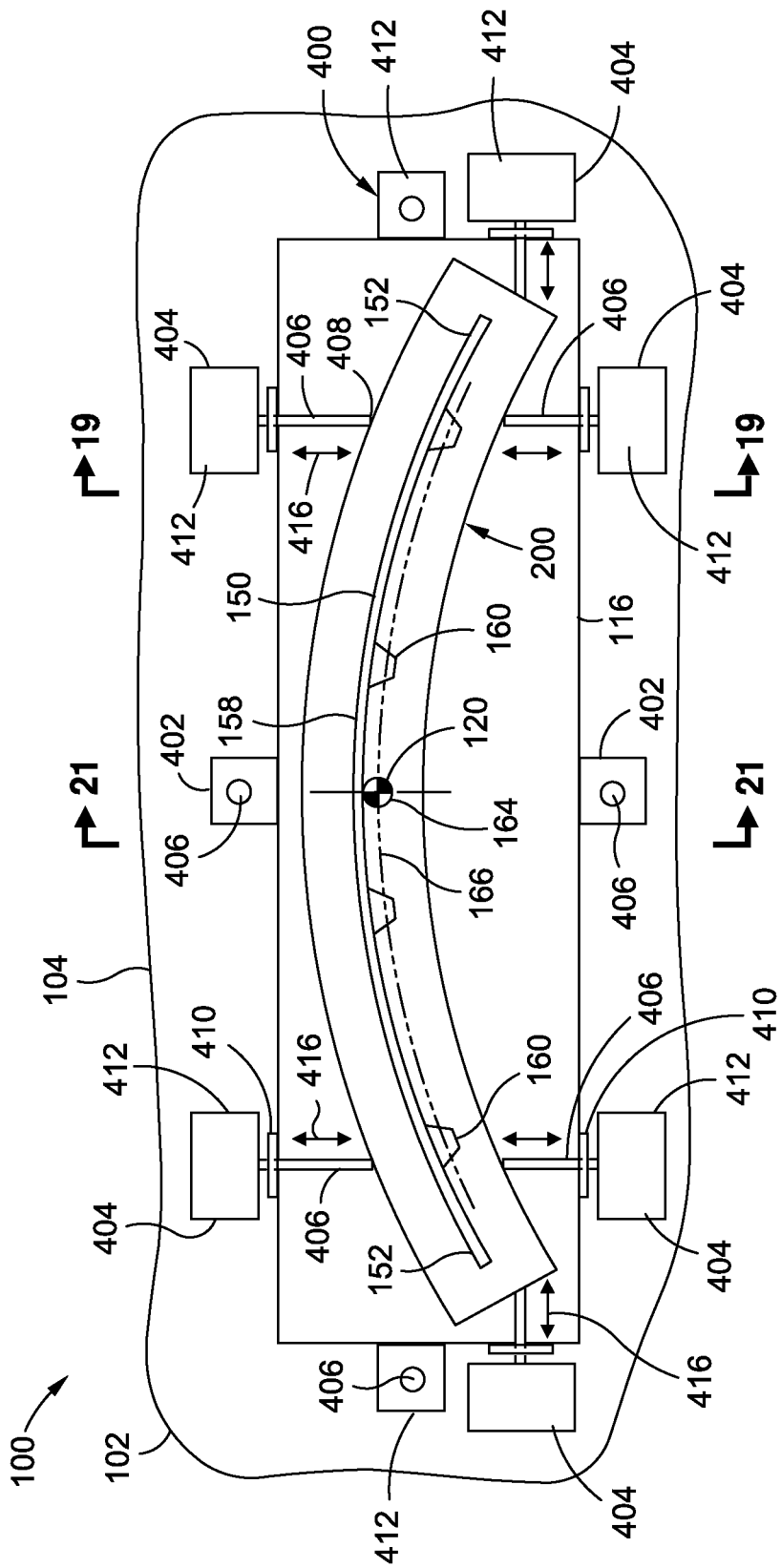
FIG. 18 is a top schematic view of the testing system taken along line 18 of FIG. 15 and showing of a plurality of lateral adjustment mechanisms and a plurality of vertical adjustment mechanisms for adjusting the location and/or orientation of the test panel and/or test fixture relative to the testing machine.

FIG. 18 is a top schematic view of an embodiment of the testing system 100 having a plurality of adjustment mechanisms 400 for adjusting the location and/or orientation of the test panel 150. In the example shown, the adjustment mechanisms 400 may include a plurality of vertical adjustment mechanisms 402 and a plurality of lateral adjustment mechanisms 404. Each one of the adjustment mechanisms 400 may include a threaded rod member. Each one of the rod members 406 of the lateral adjustment mechanisms 404 may have a bearing tip 408 that may be placed in bearing contact with the test panel 150 and/or with the end load element 236 on which the test panel 150 may be supported. The bearing tip 408 of the rod members 406 of each one of the vertical adjustment mechanisms 402 may be placed in bearing contact with the testing machine base 104. Although FIG. 18 illustrates four (4) vertical adjustment mechanisms 402 and six (6) lateral adjustment mechanisms 404, the alignment apparatus 300 may include any number of vertical adjustment mechanisms 402 and any number of lateral adjustment mechanisms 404, including only a single one of the vertical or lateral adjustment mechanisms 402, 404.

In some examples, the lateral adjustment mechanisms 404 may be cooperatively actuated in a manner to laterally move or relocate the test panel 150 relative to the loading axis 120. For example, the lateral adjustment mechanisms 404 may each include a motor 412 or motor controller 414 that may receive commands from the processor 320. The commands may be generated in response to a determination by the processor 320 that the test panel 150 is misaligned with the loading axis 120 of the testing machine 102. The commands may be transmitted to the motors 412 or motor controllers 414 to laterally displace the test panel 150 along a lateral direction 416 by moving the end load element 236 relative to the lower platen 116 such that the centerline 164 and/or the neutral axis 166 of the test panel 150 is moved into substantial alignment with the loading axis 120 of the testing machine 102. In a similar manner, one or more of the vertical adjustment mechanisms 402 may receive one or more commands from the processor 320 to vertically adjust the height of one or more sides of the lower platen 116 relative to the testing machine base 104 as a means to change the orientation of the test panel 150 such that the centerline 164 and/or neutral axis 166 of the test panel 150 is moved into substantial alignment with the loading axis 120 of the testing machine 102.

Figure 19:
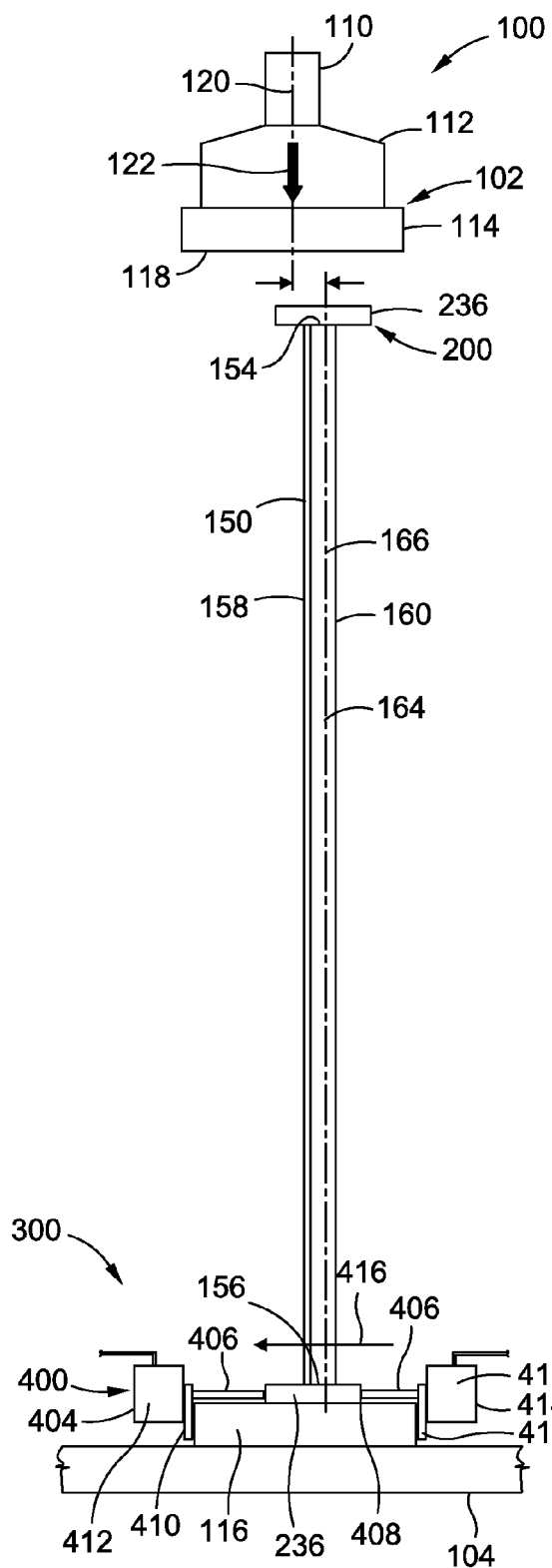
FIG. 19 is a side sectional view of the test panel/test fixture taken along line 19 of FIG. 18 and showing a neutral axis of the test panel misaligned with the loading axis.

FIG. 19 is a side view of the test panel 150/test fixture 200 showing the test panel 150 neutral axis 166 being offset or misaligned with the loading axis 120 of the testing machine 102. Also shown are the pair of lateral adjustment mechanisms 404 coupled to the lower platen 116. Each one of the adjustment mechanisms 400 includes a threaded rod member 406 that may be threadably engaged to the lower platen 116 by a bracket 410. As indicated above, each one of the threaded rod members 406 may have a bearing tip 408 in contact with the lower end load element 236 which supports the test panel 150. Each one of the lateral adjustment mechanisms 404 may be operated by a motor 412 that may be communicatively coupled to the processor 320 (FIG. 15). As indicated above, the laser scanners 314 (FIG. 15) may scan the surfaces and edges of the test panel 150 and may transmit the scanning data to the data acquisition device 318 which, in turn, may transmit the scanning data to the processor 320. The processor 320 may determine the location of the neutral axis 166 of the test panel 150 relative to the loading axis 120 based upon the scanning data.

Figure 20:
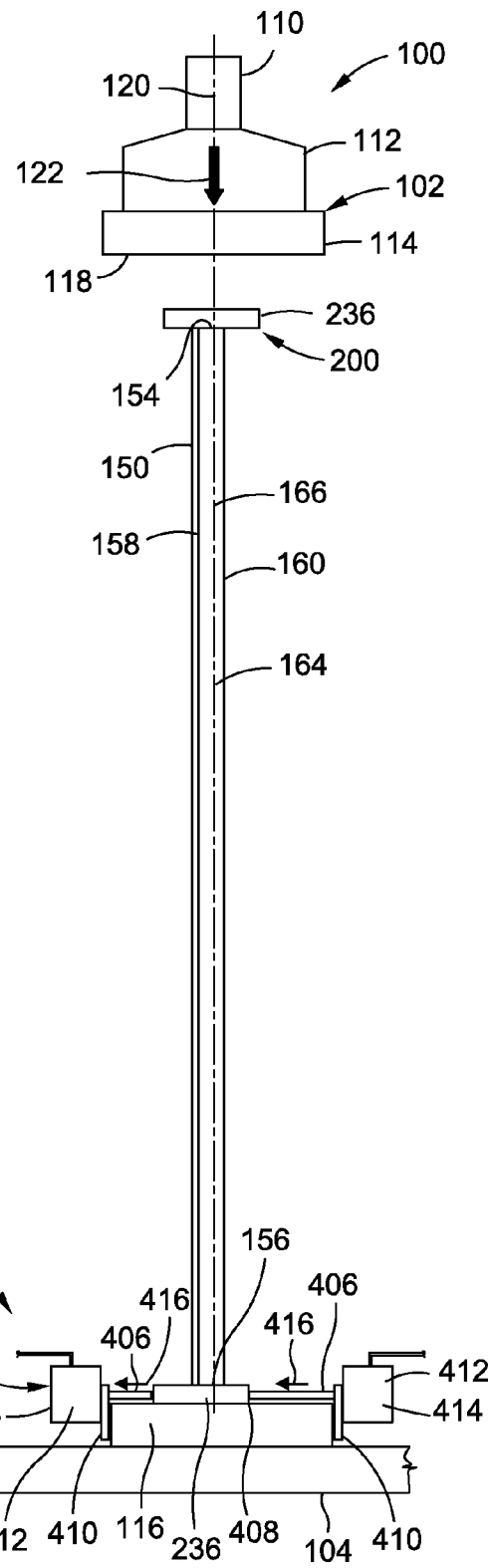
FIG. 20 is a side sectional view of the test panel/test fixture following the adjustment of the lateral position of the test panel by using the lateral adjustment mechanisms such that the neutral axis of the test panel is aligned with the loading axis of the testing machine.

FIG. 20 is a side view of the test panel 150 showing the test panel 150 neutral axis 166 moved into alignment with the loading axis 120 of the testing machine 102. Also shown are the pair of lateral adjustment mechanisms 404 coupled to the lower platen 116. The motors 412 of the lateral adjustment mechanisms 404 may be activated upon command by the processor 320 to cooperatively move the test panel 150. For example, the motors 412 of each one of the lateral adjustment mechanisms 404 may be configured to rotate the horizontally-oriented threaded rod member 406 to laterally displace the lower end load element 236 supporting the test panel 150. After the neutral axis 166 is moved into alignment with a loading axis 120 of the testing machine 102, the bearing tips 408 of the opposing threaded rod members 406 may remain in contact with the end load element to stabilize the lateral position of the test panel 150 during application of the compressive test load 122.

Figure 21:
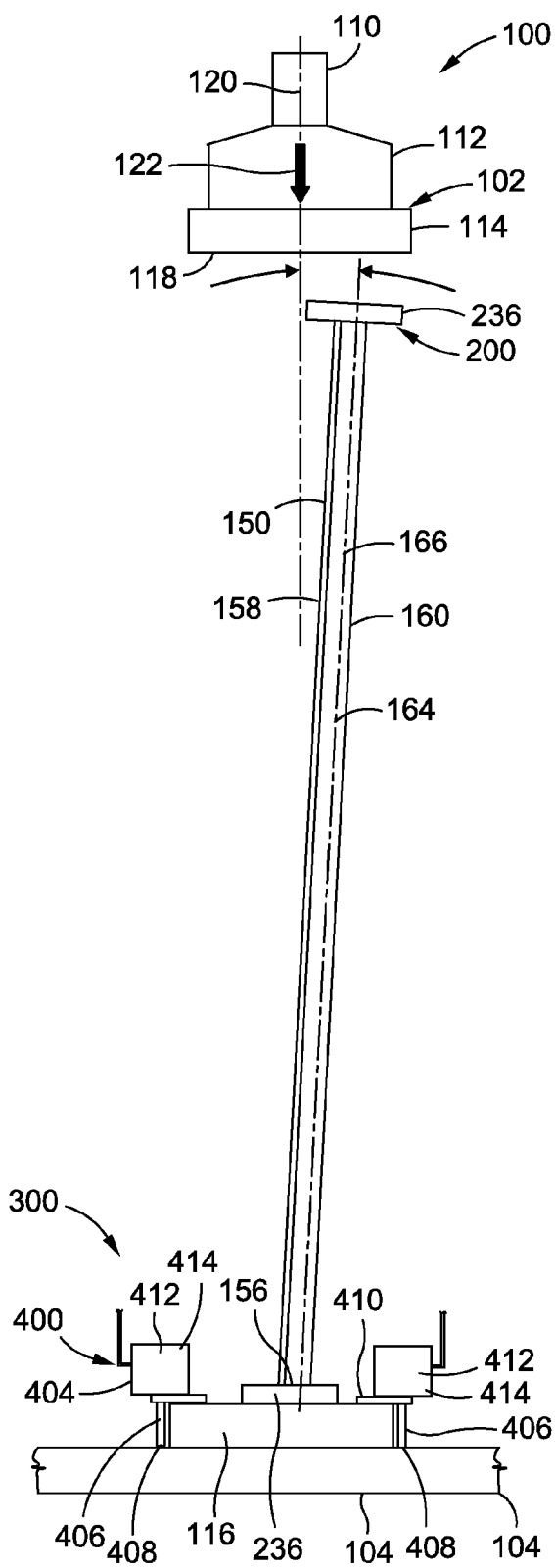
FIG. 21 is a side sectional view of the test panel/test fixture taken along line 21 of FIG. 18 and showing the neutral axis of the test panel oriented at an angle relative to the loading axis.

FIG. 21 is a side view of the test panel 150/test fixture 200 showing the neutral axis 166 of the test panel 150 oriented at an exaggerated angle relative to the loading axis 120. Also shown are a pair of the vertical adjustment mechanisms 402 coupled to the lower platen 116. The motors 412 of one or more of the vertical adjustment mechanisms 402 may be activated upon command by the processor 320 to cooperatively tilt the test panel 150. The motors 412 of a vertical adjustment mechanism 402 may rotate the vertically-oriented threaded rod member 406 to vertically displace one side of the end load element 236 until the neutral axis 166 of the test panel 150 is moved into alignment with the loading axis 120 of the testing machine 102.

Figure 22:
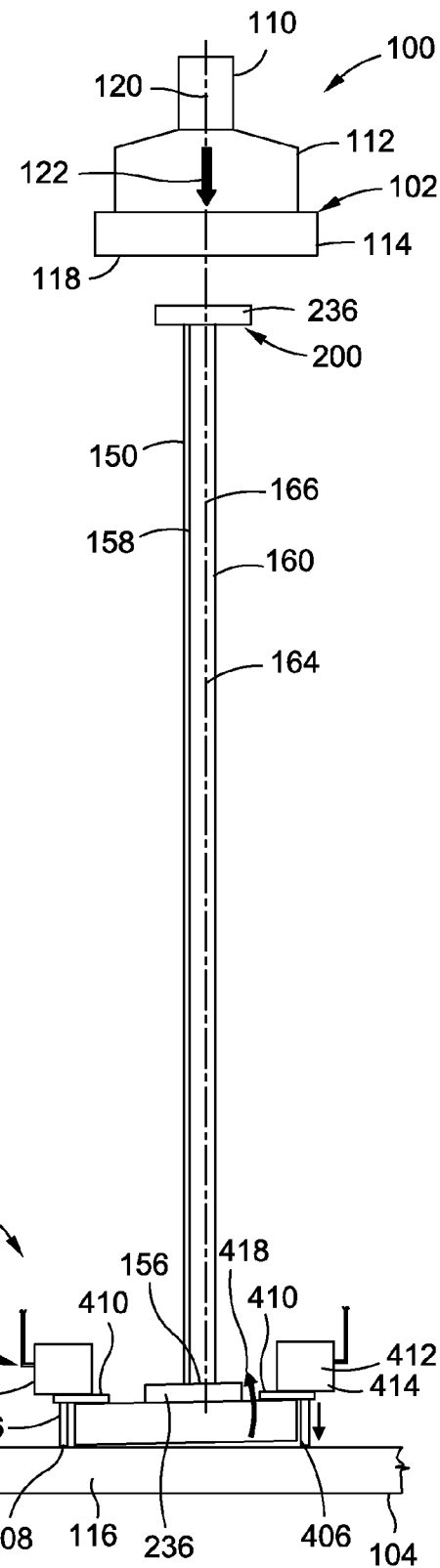
FIG. 22 is a side sectional view of the test panel/test fixture following the adjustment of the test panel orientation using the vertical adjustment mechanisms to bring the neutral axis of the test panel into alignment with the loading axis.

FIG. 22 is a side view of the test panel 150/test fixture 200 following the adjustment of the test panel 150 orientation using the vertical adjustment mechanisms 402 to bring the neutral axis 166 of the test panel 150 into alignment with the loading axis 120. Following alignment of the neutral axis 166 with the loading axis 120, shims 248 may optionally be installed in the gap 238 between the lower platen 116 and the testing machine base 104 to stabilize the lower platen 116 against movement during application to compressive test load 122. In some examples, the laser scanner 314 may continuously scan the surface geometry of the test panel 150 during application of the compressive test load 122 and may record measurement of the orientation and/or location of the test panel 150 relative to the testing machine 102.

Figure 23:
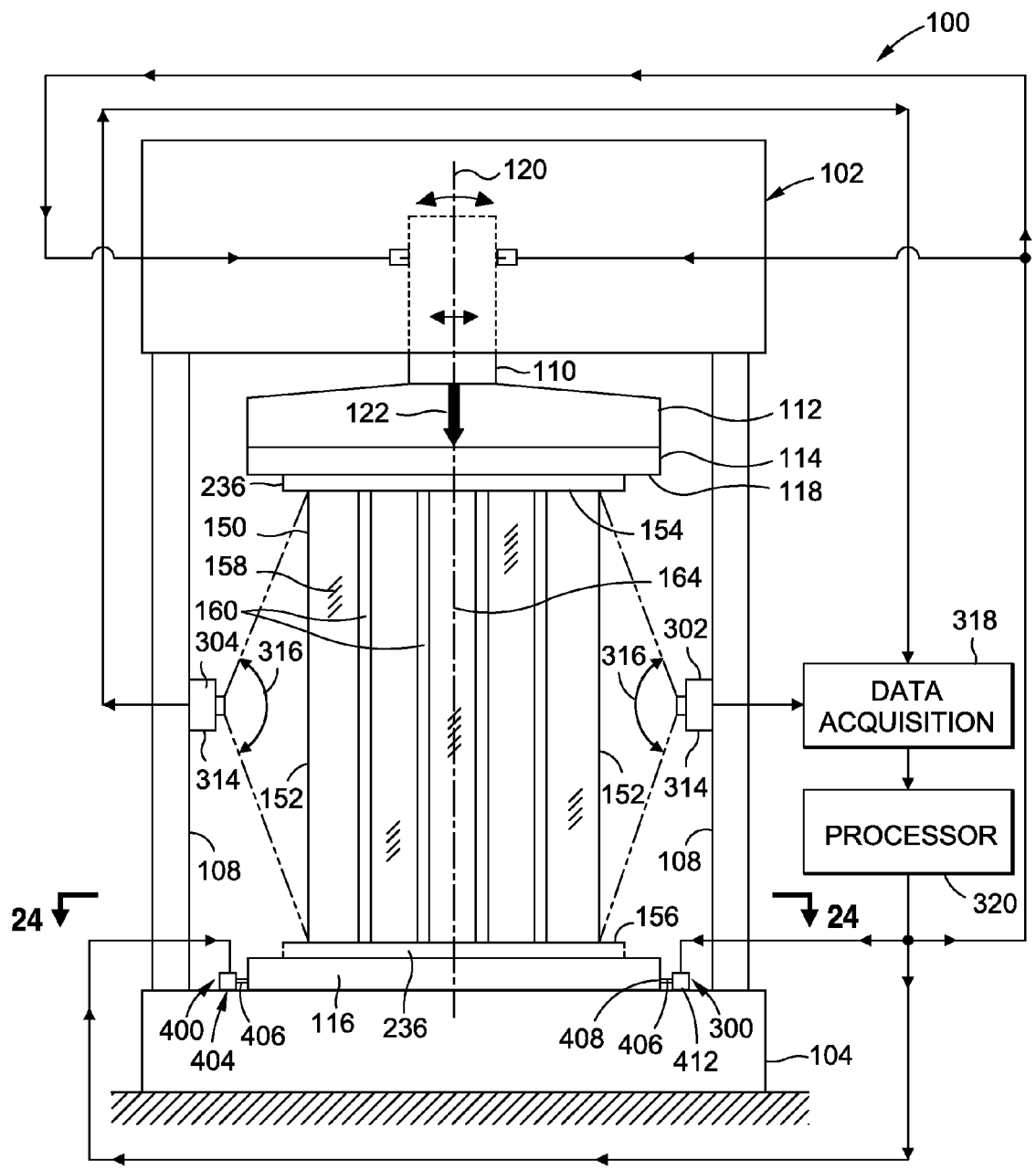
FIG. 23 is a front view of an alternative embodiment of a testing system having adjustment mechanisms incorporated into the testing machine and configured for adjusting the components of the testing machine for aligning the test panel with the loading axis and/or a platen.

FIG. 23 shows an alternative embodiment of a testing system 100 having adjustment mechanisms 400 configured for adjusting one or more components of the testing machine 102 as a means to align the test panel 150 with the loading axis 120 and/or the upper platen 114 of the testing machine 102. In the embodiment shown, the testing machine 102 may include one or more adjustment mechanisms 400 configured for adjusting the lateral position and/or the angular orientation of the shaft 110 to which the upper platen 114 is mounted. For example, one or more adjustment mechanisms 400 may be operatively engaged to the shaft 110 extending upwardly into the cross head 106. The adjustment mechanisms 400 may be configured similar to the adjustment mechanisms 400 shown in FIG. 14 and described above. However, in any of the embodiments disclosed herein, the adjustment mechanisms 400 may be provided in any configuration capable of adjusting the lateral position, vertical position, and/or angular orientation of any component of the testing machine 102 or test fixture 200, and are not limited to the arrangement of the adjustment mechanism 400 shown in FIG. 14.

In FIG. 23, the adjustment mechanisms 400 may be configured to adjust the position and or angular orientation of the shaft 110 such that the compressive test load 122 is substantially aligned with the neutral axis 166 and/or the vertical centerline 164 of the test panel 150. The testing machine 102 may also include one or more adjustment mechanisms 400 coupled to the testing machine base 104 and configured to position and/or tilt or angular orientation of the lower platen 116 based upon commands generated by the processor 320 in response to laser measurement data provided by the laser scanners 314, in a manner as described above.

Figure 24:
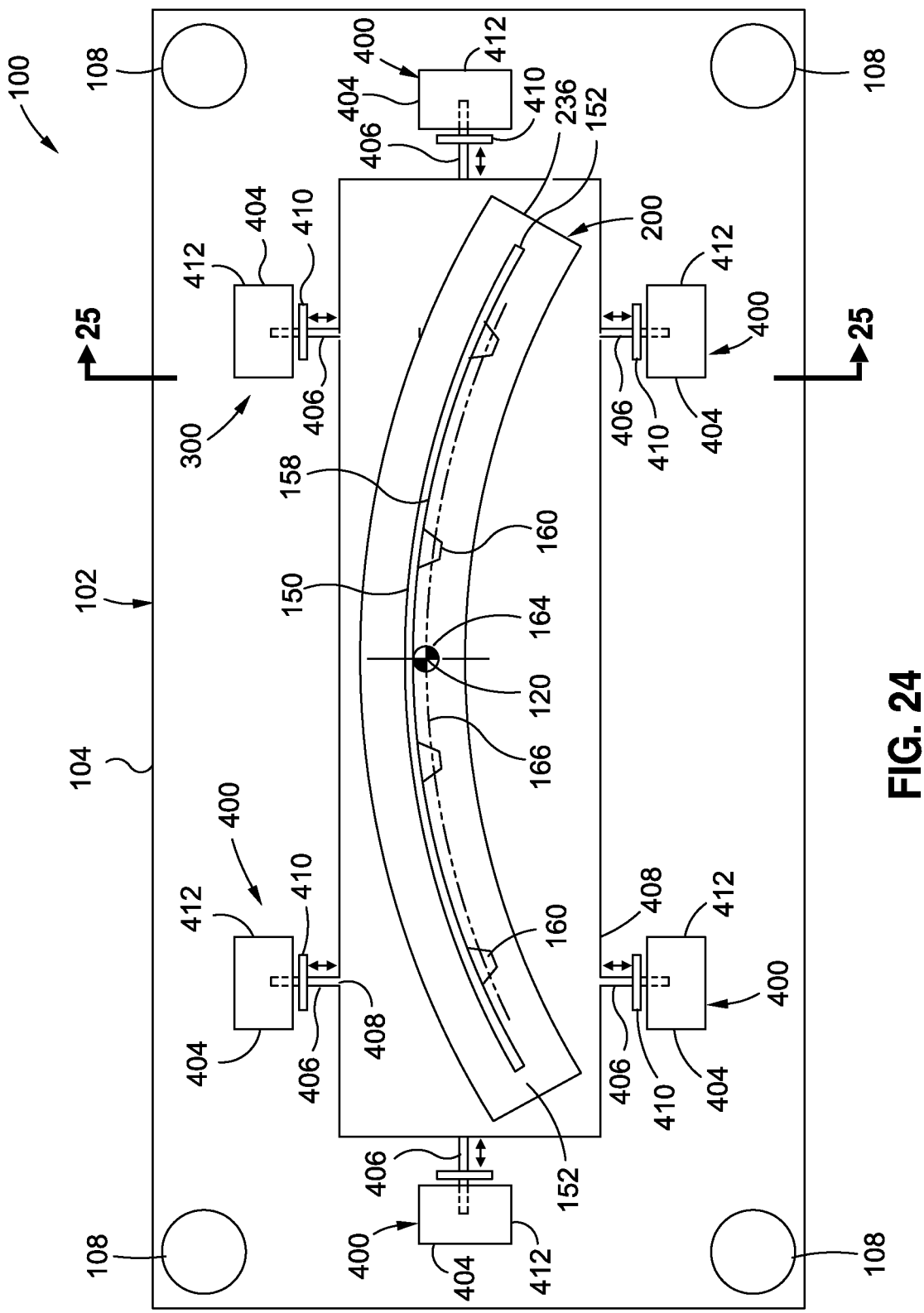
FIG. 24 is a sectional view of the testing machine taken along line 24 of FIG. 23 and illustrating an example of lateral adjustment mechanisms mounted to the testing machine base and configured for moving the lower platen.

FIG. 24 shows an example of an arrangement of a plurality of adjustment mechanisms 400 coupled to the testing machine base 104 and configured for adjusting the lateral position of the lower platen 116 relative to the testing machine base 104. In an embodiment, each one of the adjustment mechanism 400 may be fixedly coupled to the testing machine base 104 and may include a threaded rod member 406 extending through a threaded bore formed in a mounting bracket 410 mounted to the testing machine base 104. The processor 320 may be configured to generate commands to one or more of the adjustment mechanisms 400 so that the adjustment mechanisms 400 may be operated in a coordinated manner to laterally displace the lower platen 116 relative to the testing machine base 104. In other embodiments, the testing machine 102 may include adjustment mechanisms 400 configured for adjusting the angular orientation of the lower platen 116 by means of vertically displacing one or more sides of the lower platen 116 in a manner shown in FIGS. 21-22 and described above.

Figure 25:
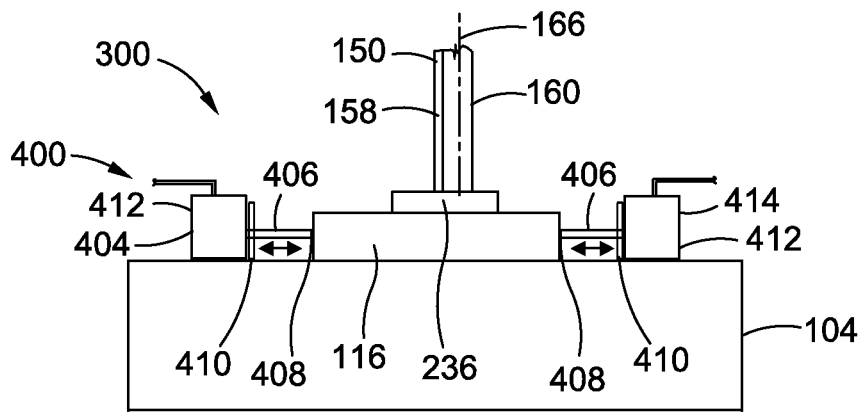
FIG. 25 is a side sectional view of the testing machine taken along line 25 of FIG. 24 and illustrating an arrangement of the lateral adjustment mechanisms for adjusting the position of the lower platen.

FIG. 25 is a side view of the testing machine 102 showing an arrangement of the lateral adjustment mechanisms 400 for adjusting the lateral position of the lower platen 116. In the embodiment shown, each one of the adjustment mechanisms 400 made include a threaded rod member 406 having a bearing tip 408 that may be placed in contact with the lower platen 116 such as a side of the lower platen 116. Based upon the laser measurement data generated by the laser scanners 314 after scanning the surface geometry of the test fixture 200 and/or test panel 150, the processor 320 may generate commands that may be transmitted to the motor controllers 414 (e.g., FIG. 14) of the adjustment mechanisms 400.

Figure 26:
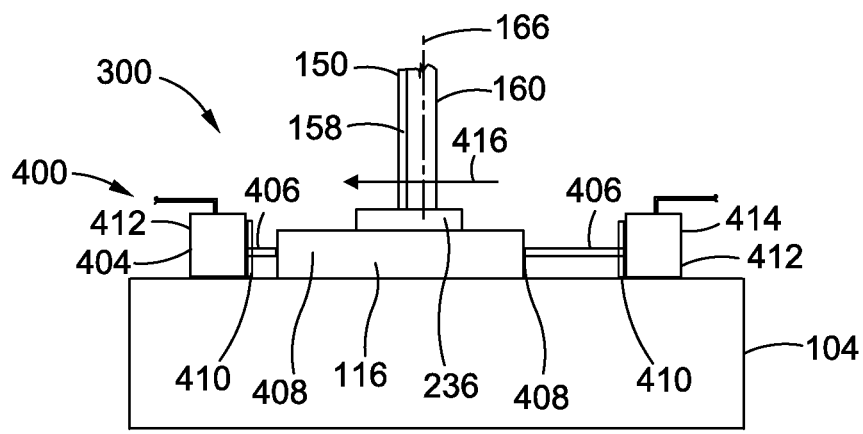
FIG. 26 is a side sectional view of the testing machine following the adjustment of the position of the lower platen relative to the testing machine base using the adjusting mechanisms.

FIG. 26 is a side sectional view of the testing machine 102 showing the adjustment of the lateral position of the lower platen 116 relative to the testing machine base 104 using the adjusting mechanisms 400. The adjustment mechanisms 400 may be operated in a coordinated manner such that the neutral axis 166 and/or vertical centerline 164 of the test panel 150 is moved into substantial alignment with the loading axis 120 of the testing machine 102. As indicated above, the testing system 100 may be configured such that the adjustment mechanisms 400 are operated in an autonomous manner in response to commands generated by the processor 320 based upon the laser measurement data from the laser scanners 314.

Figure 27:
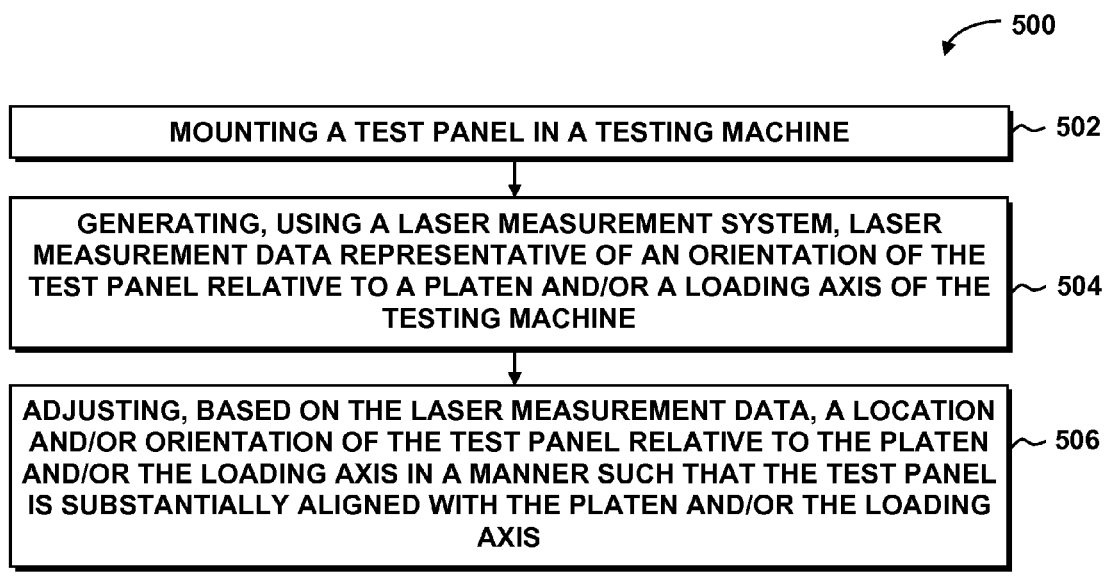
FIG. 27 is a flow chart having one or more operations that may be included in a method of aligning a test panel with a testing machine.

FIG. 27 is a flow chart having one or more operations that may be included in a method of aligning a test panel 150 with a testing machine 102. In some examples, the method 500 may be implemented after installing the test panel 150 in a testing machine 102 and prior to applying a compressive test load 122 to the test panel 150. In some embodiments, one or more of the operations described below may be implemented during application of the compressive test load 122 to the test panel 150.

Step 502 of the method 500 of FIG. 27 may include mounting the test panel 150 in a testing machine 102. In some examples, the test panel 150 may be loaded in the testing machine 102 without the use of a test fixture 200 as shown in FIG. 13. For example, the lower panel edge 156 of the test panel 150 may be supported on a lower end load element 236 which, in turn, may be supported on a lower platen 116 of the testing machine 102. The upper panel edge 154 of the test panel 150 may include an upper end load element 236 to act as an interface with the upper platen 114. In other examples, the test panel 150 may be supported in a test fixture 200 such as the test fixture 200 illustrated in FIGS. 1-5. The test fixture 200 may then be loaded into the testing machine 102 such that the base assembly 240 of the test fixture 200 is supported on the lower platen 116 of the testing machine 102. During alignment of the test panel 150, the upper platen 114 may be positioned in spaced relation to a load transmitting interface 202 which may be mounted on the upper panel edge 154 as shown in FIGS. 6-9.

Step 504 of the method 500 of FIG. 27 may include generating laser measurement data representative of the orientation of the test panel 150 relative to a platen and/or a loading axis 120 of the testing machine 102. The laser measurement data may be generated by a laser measurement system 302 which may include one or more laser measuring devices 304. In some examples, the laser measuring devices 304 may be coupled to the test fixture 200 and/or to the testing machine 102. In other examples, one or more of the laser measuring devices 304 may be mounted off of the testing machine 102 such as on other structure located near the testing machine 102.

Step 506 of the method 500 of FIG. 27 may include adjusting the location and/or the orientation of the test panel 150 relative to a platen and/or a loading axis 120 of the testing machine 102 based on the laser measurement data. The location and/or the orientation of the test panel 150 may be adjusted in a manner such that the test panel 150 is substantially aligned with the platen and/or the loading axis 120. In some examples, the test panel 150 may include an upper panel edge 154 upon which a load transmitting interface 202 may be mounted. The load transmitting interface 202 may include a first end portion 208 and a second end portion 210 as illustrated in FIG. 5 and indicated above. In such examples, the method may include adjusting one or more of the adjustment mechanisms 400 to raise and/or lower the first end portion 208 and/or the second end portion 210 of the test panel 150 in order to tilt the test panel 150 in a manner to substantially align the load transmitting interface 202 with the platen 114. In this regard, the method may include generating laser measurement data representative of the orientation of the upper panel edge 154 relative to the upper platen 114 of the testing machine 102, and based on the laser measurement data, the method may include adjusting the orientation of the test panel 150 such that the upper panel edge 154 is substantially aligned with or is oriented parallel to the upper platen 114.

In other examples, the method may include generating laser measurement data representative of the location and/or the orientation of a longitudinal (e.g., vertical) centerline 164 of the test panel 150 relative to the loading axis 120. For example, the laser measurement system 302 may include a plurality of laser scanners 314 that may be configured to scan the surfaces and edges of the test panel 150 and determine the location of the centerline 164 of the test panel 150 based on the scanning. The alignment apparatus 300 may be configured to adjusting the orientation of the test panel 150 based on the laser measurement data in a manner such that the centerline 164 is substantially aligned with the loading axis 120. In the present disclosure, the centerline 164 of the test panel 150 may be defined as a vertical centerline located midway between opposite side 152 edges of the test panel 150.

In a further embodiment, the method may include generating laser measurement data representative of the location of the neutral axis 166 of the test panel 150 relative to the loading axis 120. For example, the curved test panel 150 with stiffeners 160 shown in FIG. 15 may include a neutral axis 166 that may be offset from a mid-plane of the skin panel 158 to which the stiffeners 160 are coupled. Advantageously, the method may include scanning the surface geometry of the stiffeners 160 and skin panel 158 using the laser scanners 314, and determining the location of the neutral axis 166 relative to the loading axis 120 using the scanning data. The method may further include processing the laser measurement data and adjusting the location and/or orientation of the test panel 150 such that the loading axis 120 passes through the neutral axis 166 as in FIG. 18. As indicated above, some embodiments of the alignment apparatus 300 may include motorized adjustment mechanisms 400 having motors 412 which may be communicatively coupled to the processor 320. In such an embodiment, the method may include receiving the laser measurement data at the processor 320, and commanding the motors 412 of the adjustment mechanisms 400 to move (e.g., laterally displace, tilt) the test panel 150 into substantial alignment with the platen and/or the loading axis 120. The adjustment mechanisms 400 may be operated in a manner to adjust the orientation of the test panel 150 by adjusting the position and/or the orientation of the test fixture relative to a platen 114, 116 and/or the loading axis 120, by adjusting the position and/or the orientation of one or more platens 114, 116 relative to the testing machine base 104 or crosshead 106, and/or by adjusting the angular orientation of the loading axis 120 relative to the testing machine 102.

As indicated above, the method may further include using one or more laser scanners 314 to scan the surface geometry of the test panel 150 and/or the test fixture 200, and generate scanning data that may be representative of the surface geometry. The method may further include receiving the scanning data at a processor 320 and determining the location and/or the orientation of the test panel 150 relative to a platen and/or a loading axis 120 of the testing machine 102 based on the scanning data. In this regard, the method may include commanding the motors 412 of one or more of the adjustment mechanisms 400 to move the test panel 150 into substantial alignment with the platen and/or the loading axis 120.

Additional modifications and improvements of the present disclosure may be apparent to those of ordinary skill in the art. Thus, the particular combination of parts described and illustrated herein is intended to represent only certain embodiments of the present disclosure and is not intended to serve as limitations of alternative embodiments or devices within the spirit and scope of the disclosure.

What is claimed is:

1. An alignment apparatus for aligning a test panel with a testing machine, comprising:
   a laser measuring system including at least one laser measuring device coupled to at least one of a test fixture and a testing machine and configured to generate laser measurement data representative of an orientation of a test panel relative to a platen and a loading axis of the testing machine; and
   an adjustment mechanism configured to adjust, based on the laser measurement data, a location or orientation of the test panel relative to the platen and the loading axis in a manner such that the test panel is moved into substantially alignment with the platen and the loading axis such that a compressive test load is substantially uniformly distributed across a panel edge of the test panel.

2. The alignment apparatus of claim 1, wherein:
   the laser measuring device is configured to generate laser measurement data representative of an orientation of a panel edge of the test panel relative to the platen.

3. The alignment apparatus of claim 1, wherein:
   the laser measuring device is configured to generate laser measurement data representative of a location or orientation of at least one of a centerline and a neutral axis of the test panel relative to the loading axis.

4. The alignment apparatus of claim 1, further comprising:
   a processor configured to receive the laser measurement data from the laser measuring device;
   a motor operatively coupled to the adjustment mechanism and communicatively coupled to the processor; and
   the processor being configured to generate a command based on the laser measurement data to operate the adjustment mechanism in a manner such that the test panel is moved into substantial alignment with the platen and the loading axis.

5. The alignment apparatus of claim 1, further comprising:
   a processor;
   the laser measuring device is a laser scanner communicatively coupled to the processor and configured to scan a surface geometry of at least one of the test panel and the test fixture and generate scanning data representative of the surface geometry; and
   the processor being configured to receive the scanning data from the laser scanner and determine a location or orientation of the test panel relative to the platen and the loading axis based on the scanning data.

6. The alignment apparatus of claim 5, further comprising:
   a motor operatively coupled to the adjustment mechanism and communicatively coupled to the processor;
   the processor being configured to determine at least one of the location and orientation of a neutral axis of the test panel relative to the loading axis based on the scanning data; and
   the processor being configured to command the motor to operate the adjustment mechanism in a manner such that the neutral axis of the test panel is moved into substantial alignment with the loading axis.

7. The alignment apparatus of claim 1, wherein the adjustment mechanism is configured to adjust at least one of the following:
   at least one of a position and an orientation of a test fixture relative to the platen and the loading axis;

at least one of a position and an orientation of the platen and the loading axis relative to the testing machine.

8. The alignment apparatus of claim 1, wherein:
the adjustment mechanism includes a threaded rod member threadably coupled to a base assembly of a test fixture; and
the threaded rod member having a bearing tip in contact with a lower platen, rotation of the threaded rod member resulting in axial movement thereof relative to the base assembly causing displacement of the base assembly.

9. An alignment apparatus for a compression testing system having a platen for applying a compressive test load to a test panel, comprising:
a load transmitting interface configured to be positioned on a panel edge of a test panel;
a first and a second laser measuring device disposed on a respective first and second end portion of the load transmitting interface, the first and second laser measuring device being configured to determine a value indicative of a respective first and second distance between the platen and the respective first and second end portion; and
an adjustment mechanism disposed on a base assembly of a test fixture and configured to adjust an orientation of the test panel by raising or lowering at least one of a first end portion and the second end portion of the load transmitting interface to substantially equalize the first and second distances in a manner such that the load transmitting interface is aligned with the panel edge such that a compressive test load is uniformly distributed across a first side edge of the test panel.

10. A method of aligning a test panel in a testing machine for applying a compressive test load to the test panel, comprising the steps of:
mounting a test panel in a testing machine;
generating, using a laser measuring device coupled to at least one of a test fixture and the testing machine, laser measurement data representative of an orientation of the test panel relative to a platen and a loading axis of the testing machine; and
adjusting, based on the laser measurement data, a location or orientation of the test panel relative to the platen and the loading axis in a manner such that the test panel is substantially aligned with the platen and the loading axis.

11. The method of claim 10, wherein the step of adjusting the orientation of the test panel includes:
adjusting at least one of a position and an orientation of a test fixture relative to the platen and the loading axis;
adjusting at least one of a position and an orientation of the platen and the loading axis relative to the testing machine.

12. The method of claim 10, wherein the test panel includes a panel edge having a load transmitting interface mounted thereon, the step of adjusting the orientation of the test panel includes:
adjusting an adjustment mechanism coupled to the test fixture to raise or lower at least one of a first end portion and a second end portion of the test panel in a manner to substantially align the load transmitting interface with the platen.

13. The method of claim 10, wherein the steps of generating the laser measurement data and adjusting the test panel comprise:
generating laser measurement data representative of an orientation of a panel edge relative to a platen of the testing machine; and
adjusting, based on the laser measurement data, the orientation of the test panel such that the panel edge is substantially aligned with the platen.

14. The method of claim 10, wherein the steps of generating the laser measurement data and adjusting the test panel comprise:
generating laser measurement data representative of at least one of a location and orientation of a centerline of the test panel relative to the loading axis; and
adjusting, based on the laser measurement data, the orientation of the test panel such that the centerline is substantially aligned with the loading axis.

15. The method of claim 10, wherein the steps of generating the laser measurement data and adjusting the test panel comprise:
generating laser measurement data representative of a location of a neutral axis of the test panel relative to the loading axis; and
adjusting, based on the laser measurement data, the orientation of the test panel such that the loading axis passes through the neutral axis.

16. The method of claim 10, wherein a motor is operatively coupled to an adjustment mechanism, the steps of generating the laser measurement data and adjusting the test panel comprising:
receiving the laser measurement data at a processor communicatively coupled to the motor; and
commanding, using the processor, the motor to adjust an adjustment mechanism in a manner to move the test panel into substantial alignment with the platen and the loading axis.

17. The method of claim 10, wherein the laser measuring device is a laser scanner communicatively coupled to a processor, the step of generating the laser measurement data comprising:
scanning, using a laser scanner, a surface geometery at least one of of the test panel and the test fixture;
generating scanning data representative of the surface geometry; and
determining, using a processor, a location or orientation of the test panel relative to the platen and the loading axis based on the scanning data.

18. The method of claim 17, wherein the step of adjusting the location or orientation of the test panel includes:
commanding, using a processor, a motor of an adjustment mechanism in a manner to move the test panel into substantial alignment with the platen and the loading axis.

19. The method of claim 18, wherein the steps of generating the laser measurement data and adjusting the test panel comprising:
determining, using the processor based on the scanning data, a location of a neutral axis of a test panel having stiffeners coupled to a skin panel; and
commanding, using a processor, a motor to adjust an adjustment mechanism in a manner to move the test panel such that the loading axis passes through the neutral axis.

20. The method of claim 18, wherein:
the adjustment mechanism comprises at least one of a vertical adjustment mechanism and a lateral adjustment mechanism configured to adjust a location or orientation of the test panel relative to the platen and the loading axis.

* * * * *